United States Patent
Rupprecht et al.

[11] Patent Number: 5,284,840
[45] Date of Patent: Feb. 8, 1994

[54] ALKYLIDENE MACROLIDES HAVING IMMUNOSUPPRESSIVE ACTIVITY

[75] Inventors: Kathleen Rupprecht; Robert Baker, both of Cranford, N.J.

[73] Assignee: Merck & Co., Inc., Rahway, N.J.

[21] Appl. No.: 897,738

[22] Filed: Jun. 12, 1992

[51] Int. Cl.$^5$ .................. A61K 31/395; C07D 267/00
[52] U.S. Cl. ........................... 514/183; 514/291; 514/411; 540/455; 540/456
[58] Field of Search ............... 540/456, 455; 514/183, 514/291, 411

[56] References Cited

U.S. PATENT DOCUMENTS

| | | | |
|---|---|---|---|
| 4,894,366 | 1/1990 | Okuhara et al. | 514/63 |
| 4,929,611 | 5/1990 | Okuhara et al. | 514/183 |
| 4,956,352 | 9/1990 | Okuhara et al. | 514/63 |
| 4,981,792 | 1/1991 | Inamine et al. | 435/119 |
| 5,011,844 | 4/1991 | Fehr | 514/291 |
| 5,064,835 | 11/1991 | Bochis et al. | 514/291 |
| 5,110,811 | 5/1992 | Okuhara et al. | 514/183 |

FOREIGN PATENT DOCUMENTS

| | | |
|---|---|---|
| 0349061 | 1/1990 | European Pat. Off. |
| 0353678 | 2/1990 | European Pat. Off. |
| 0388152 | 9/1990 | European Pat. Off. |
| 0402931 | 12/1990 | European Pat. Off. |
| 0413532 | 2/1991 | European Pat. Off. |
| 0427680 | 5/1991 | European Pat. Off. |
| 0428365 | 5/1991 | European Pat. Off. |
| 0463690 | 1/1992 | European Pat. Off. |

(List continued on next page.)

OTHER PUBLICATIONS

Tanaka, et al., J. Am. Chem. Soc., 1987, 109 5031–5033.

*Primary Examiner*—John M. Ford
*Assistant Examiner*—Y. N. Gupta
*Attorney, Agent, or Firm*—Charles M. Caruso; J. Eric Thies

[57] ABSTRACT

Alkylidene macrolides of the general structural Formula I:

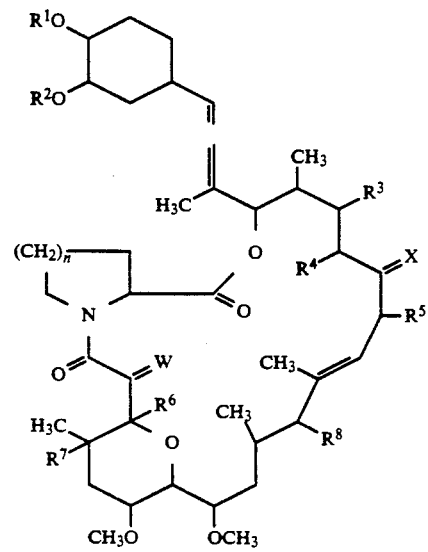

have been prepared from suitable precursors by derivitization at C-9 or C-22. These macrolide immunosuppressants are useful in a mammalian host for the treatment of autoimmune diseases, infectious diseases and/or the prevention of rejection of foreign organ transplants. In addition, these macrolide immunosuppressants are useful in the topical treatment of inflammatory and hyperproliferative skin diseases and cutaneous manifestations of immunologically-mediated illnesses. Also, these macrolides are useful in the treatment of reversible obstructive airways disease, particularly asthma; as hair revitalizing agents, especially in the treatment of male pattern alopecia oralopecia senilis; in the reversal of multidrug resistance of tumor cells; in treatment of inflammation of mucosa and blood vessels, gastric ulcers, vascular damage, ischemic bowel disease, inflammatory bowel disease, necrotizing entercolitis, intestinal lesions associated with thermal burns; in the treatment of cytomegalovirus infection; and in the treatment of idiopathic thrombocytopenic purpura and Basedow's disease.

8 Claims, No Drawings

ALKYLIDENE MACROLIDES HAVING IMMUNOSUPPRESSIVE ACTIVITY

SUMMARY OF THE INVENTION

The present invention is related to alkylidene macrolides which are useful in a mammalian host for the treatment of autoimmune diseases (such as juvenile-onset diabetes mellitus, multiple sclerosis and rheumatoid arthritis), immunodepression, infectious diseases and/or the prevention of rejection of foreign organ transplants, e.g. bone marrow and heart transplants and are also useful in the topical treatment of inflammatory and hyperproliferative skin diseases and cutaneous manifestations of immunologically-mediated illnesses (such as: psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus, Alopecia areata), male pattern alopecia, alopecia senilis, reversible obstructive airways disease, particularly asthma, alopecia, inflammation of mucosa and blood vessels, cytomegalovirus infection, multidrug resistance, idiopathic thrombocytopenic purpura, and/or hepatic injury associated with ischemia. In addition, some of the compounds of this invention may have antagonistic properties and so have utility in the reversal of immunosuppressive activity and/or diminishing the toxicity of other immunosuppressive agents.

More particularly, this invention relates to compounds of the general structural formula I:

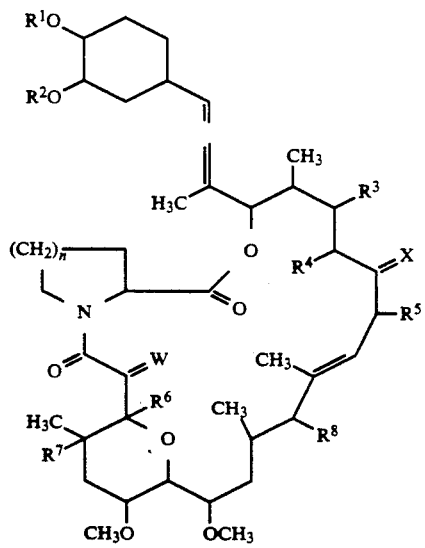

wherein $R^1$, $R^2$, $R^3$, $R^4$, $R^5$, $R^6$, $R^7$, $R^8$, W, X and n are hereinafter defined.

This invention also relates to pharmaceutical compositions containing the compounds and to a method of use of the present compounds and other agents for the treatment of and prevention of certain afflictions, diseases and illnesses.

BRIEF DESCRIPTION OF DISCLOSURES IN THE ART

Fujisawa United States European and Japanese patents and applications (U.S. Pat. No. 4,894,366, issued Jan. 16, 1990, EPO Publication No. 0,184,162 and PBJ Disclosure 63-17884) and publications (J. Am. Chem. Soc., 1987, 109, 5031 and J. Antibiotics 1987, 40, 1249) disclose 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (FR-900506), (FK-506), (L-679,934), 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (FR-900520) and related compounds which are the starting materials for the preparation of the compounds described. The synthetic preparation of the aforementioned starting material (FR-900506) has recently been reported (J. Am. Chem. Soc., 1989, 111, 1157). A Sandoz European patent application (EPO Publication No. 0,356,399) discloses stereoisomers of FR-900506 and derivatives at the 17-position. Fisons European and WIPO patent applications (EPO Publication No. 0,323,042 and PCT Publication No. WO 89/05304) discloses various derivatives of FR-900506, FR-900520 and related compounds. A Sandoz European Patent application (EPO Publication No. 0,437,680) discloses chloro, bromo, iodo and azido derivatives of FR-900506, FR-900520 and related compounds. A Merck European Patent application (EPO Publication No. 0,428,365) discloses various amino derivatives of FR-900506, FR-900520 and related compounds. A Fujisawa patent application (UK Publication No. GB 2,245,891-A) discloses various derivatives of FR-900506 bearing a heterocyclic group. Fujisawa patent applications (PCT Publication Nos. WO 92/00313 and WO 92/00980) disclose various derivatives of FR-900506 at the 17-position.

Fujisawa United States patents (U.S. Pat. No. 4,929,611, issued May 29, 1990 and U.S. Pat. No. 4,956,352, issued Sep. 11, 1990) discloses the use of FK-506-type compounds in treating resistance to transplantation. A Sandoz European patent application (EPO Publication No. 0,315,978) discloses the use of FR-900506 and related compounds in the topical treatment of inflammatory and hyperproliferative skin diseases and of cutaneous manifestations of immunologically-mediated illness. A Fisons WIPO patent application (PCT Publication No. WO 91/04025) discloses the use of various derivatives of FR-900506 in the treatment of immunodepression. A Fisons WIPO patent application (PCT Publication WO 90/14826) discloses the use of FR-900506 and related compounds in the treatment of reversible obstructive airways disease, particularly asthma. A Fujisawa European patent application (EPO Publication No. 0,423,714) discloses the use of FK-506 and derivatives as hair revitalizing agents. Various studies have suggested the efficacy of FK-506 in the treatment of a number of ailments, including rheumatoid arthitis (C. Arita, et al., Clinical exp. Immunol., 1990, 82, 456–461; N. Inamura, et al., Clin. Immunol. Immunopathol. 1988, 46, 82–90), recent-onset diabetes (N. Murase, et al., Diabetes, 1990, 39, 1584–86; N. Murase, et al., Lancet, 1990, 336, 373–74), posterior uveitis (H. Kawashima, Invest. Ophthalmol. Vis. Sci., 1988, 29, 1265–71), hepatic injury associated with ischemia (M. Sakr, et al., Life Sci., 1990, 47, 687–91) allergic encephalomyelitis (K, Deguchi, et al., Brain Nerve, 1990, 42, 391–97), glomeralonephritis (J. McCauley, et al., Lancet, 1990, 335, 674) and systemic lupus erythematosus (K. Takabayashi, et al., Clin. Immunol. Immunopathol., 1989, 51, 110–117) multidrug resistance (M. Naito, et al., *Cancer Chemother. Pharmacol.*, 1992, 29, 195–200), inflammation of mucosa and blood vessels (PCT Publication WO 91/17754), cytomegalovirus infection (UK Publication GB 2,247,620A), and idiopathic thrombocytophenic purpura and Basedow's disease (PCT Publication WO 91/19495).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Chrons disease, ulcerative colitis, bullous pemphigoid, sarcoidosis, psoriasis, ichthyosis, and Graves ophthalmophathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was approved by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, FR-900506, FK-506,

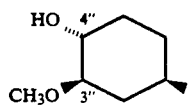

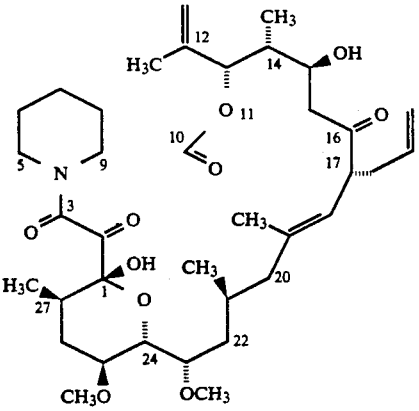
-continued (17-allky-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]-octacos-18-ene-2,3,10,16-tetraone) and related compounds which were isolated and characterized by Tanaka, Kuroda, and co-workers at Fujisawa Pharmaceutical Co. in Japan, see *J. Am. Chem. Soc.*, 1987, 109, 5031, and U.S. Pat. No. 4,894,366, issued Jan. 16, 1990) have been shown to possess exceptional immunosupressive activity. A Fujisawa U.S. patents (U.S. Pat. No. 4,929,611, issued May 29, 1990 U.S. Pat. No. 4,956,352, issued Sep. 11, 1990) disclose the use of FK-506-type compounds in treating resistance to transplantation. In particular, the compound FR-900506 has been reported to be 100 times more effective than cyclosporin in the supression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), male pattern alopecia or alopecia senilis (EPO Publication No. 0,423,714), rheumatoid arthritis (C. Arita, et al., *Clincial exp. Immunol.*, 1990, 82, 456–461; N. Inamura, et al., *Clin. Immunol. Immunopathol.* 1988, 46, 82–90), recent-onset diabetes (N. Murase, et al., *Diabetes,* 1990, 39, 1584–86; N. Murase, et al., *Lancet,* 1990, 336, 373–74), posterior uveitis (H. Kawashima, *Invest. Ophthalmol. Vis. Sci.,* 1988, 29, 1265–71), hepatic injury associated with ischemia (M. Sakr, et al., *Life Sci.,* 1990, 47, 687–91) allergic encephalomyelitis (K, Deguchi, et al., *Brain Nerve,* 1990, 42, 391–97), glomerulonephritis (J. McCauley, et al., *Lancet,* 1990, 335, 674), systemic lupus erythematosus (K. Takabayashi, et al., *Clin. Immunol. Immunopathol.,* 1989, 51, 110–117) multidrug resistance (M. Naito, et al., *Cancer Chemother, Pharmacol.,* 1992, 29, 195–200), inflammation of mucosa and blood vessels (PCT Publication WO 92/17754), cytomegalovirus infection (UK Publication GB 2,247,620A), and idiopathic thrombocytophenic purpura and Basedow's disease (PCT Publication WO 91/19495).

DETAILED DESCRIPTION OF THE INVENTION

A. Scope of the Invention

The novel compound of this invention has structural Formula I:

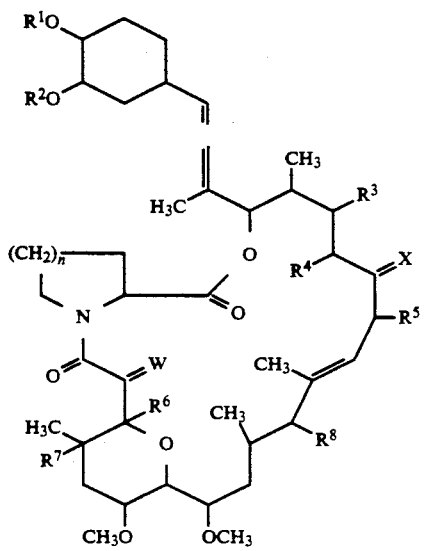

or a pharmaceutically acceptable salt thereof, wherein:

$R^1$ is selected from:
(1) hydrogen; and
(2) $C_{1-4}$ alkanoyl;

$R^2$ is selected from:
(1) methyl; and
(2) hydrogen;

$R^3$ is hydrogen, hydroxy, or $C_{1-6}$ alkoxy;

$R^4$ is hydrogen, or $R^3$ and $R^4$ taken together form a double bond;

$R^5$ is selected from:
(1) methyl,
(2) ethyl,
(3) propyl, and
(4) allyl;

$R^6$ is hydroxy or hydrogen;

$R^7$ is hydrogen, or $R^6$ and $R^7$ taken together form a double bond;

$R^8$ is hydrogen, hydroxy, or fluoro;

W and X are independently selected from:
(1) oxo,
(2) (H, OH),
(3) (OH, $R^9$), wherein $R^9$ is selected from:
 (a) $C_{1-6}$ alkyl,
 (b) $C_{2-6}$ alkenyl,
 (c) $-CH_2-SO_m-C_{1-6}$ alkyl, wherein m is 0, 1 or 2,
 (d) $-CH_2S(C_{1-6}$ alkyl$)_2{}^+M^-$, wherein $M^-$ is a negative counterion selected from: chloro, bromo, iodo,
 (e) phenyl,
 (f) furanyl,
(4) $=CR^{10}R^{11}$, wherein $R^{10}$ and $R^{11}$ are independently selected from:
 (a) hydrogen,
 (b) $C_{1-6}$ alkyl,
 (c) $C_{2-6}$ alkenyl, (d) $-SO_m-C_{1-6}$ alkyl, wherein m is as defined above;

with the proviso that W and X are not simultaneously oxo, (H, OH), or combinations thereof;

n is 1 or 2.

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

When any variable (e.g., alkyl, aryl, $R^9$, $R^{10}$, $R^{11}$, etc.) occurs more than one time in any variable or in Formula I, its definition on each ocurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec-and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy. "Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethylpentyl, and the like, and includes E and Z forms, where applicable. "Halo", as used herein, means fluoro, chloro, bromo and iodo.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium.

Preferred compounds of the present invention are the compounds identified as follows:

17-Ethyl-1,14,16-trihydroxy-12-[2'-(4"'-hydroxy-3"-methoxycyclohexyl)-1'-methylvinyl]-23,25-dimethoxy-16-methyl-13,19,21,27-tetramethyl-11,28-dioxa-4-azatricyclo[22.3.1.0$^{4,9}$]octacos-18-ene-2,3,10-trione; (1)

17-Ethyl-1,14,16-trihydroxy-12-[2'-(4"'-hydroxy-3"-methoxycyclohexyl)-1'-methylvinyl]-23,25-dimethoxy-16-methyl-13,19,21,27-tetramethyl-11,28-dioxa-4-azatricyclo[22.3.1.0$^{4,9}$]octacos-18-ene-2,3,10-trione; (2)

17-Ethyl-1,14,16-trihydroxy-12-[2'-(4"'-hydroxy-3'"-methoxycyclohexyl)-1'-methylvinyl]-23,25-dimethoxy-16-butyl-13,19,21,27-tetramethyl-11,28-dioxa-4-azatricyclo[22.3.1.0$^{4,9}$]octacos-18-ene-2,3,10-trione; (3)

17-Ethyl-1,14-dihydroxy-12-[2'-(4"'-hydroxy-3"-methoxycyclohexyl)-1'-methylvinyl]-23,25-dimethoxy-16-butyl-13,19,21,27-tetramethyl-16-methenyl-11,28-dioxa-4-azatricyclo[22.3.1.0$^{4,9}$]octacos-18-ene-2,3,10-trione; (4)

17-Ethyl-1,14-dihydroxy-12-[2'-(4''-hydroxy-3''-methoxycyclohexyl)-1'-methylvinyl]-23,25-dimethoxy-16-butyl-13,19,21,27-tetramethyl-16-(2-butenyl)-11,28-dioxa-4-azatricyclo[22.3.1.0⁴,⁹]octacos-18-ene-2,3,10-trione; (5)

17-Ethyl-1,14-dihydroxy-12-[2'-(4''-hydroxy-3''-methoxycyclohexyl)-1'-methylvinyl]-23,25-dimethoxy-16-propenyl-13,19,21,27-tetramethyl-11,28-dioxa-4-azatricyclo[22.3.1.0⁴,⁹]octacos-18-ene-2,3,10-trione; (6)

17-Ethyl-1,14,16-trihydroxy-12-[2'-(4''-hydroxy-3''-methoxycyclohexyl)-1'-methylvinyl]-23,25-dimethoxy-16-(methylthiomethyl)-13,19,21,27-tetramethyl-11,28-dioxa-a-4-azatricyclo[22.3.1.0⁴,⁹]octacos-18-ene-2,3, 10-trione; (7)

17-Ethyl-1,14,16-trihydroxy-12-[2'-(4''-hydroxy-3''-methoxycyclohexyl)-1'-methylvinyl]-23,25-dimethoxy-16-(methylsulfinylmethyl)-13,19,21,27-tetramethyl-11,28-dioxa-4-azatricyclo[22.3.1.0⁴,⁹]octacos-18-ene-2,3,10-trione; (8)

17-Ethyl-1,14,16-trihydroxy-12-[2'-(4''-hydroxy-3''-methoxycyclohexyl)-1'-methylvinyl]-23,25-dimethoxy-16-(methylsulfinylmethenyl)-13,19,21,27-tetramethyl-11, 28-dioxa-4-azatricyclo[22.3.1.0⁴,⁹]octacos-18-ene-2,3, 10-trione; (9)

17-Ethyl-1,14,16-trihydroxy-12-[2'-(4''-hydroxy-3''-methoxycyclohexyl)-1'-methylvinyl]-23,25-dimethoxy-16-phenyl-13,19,21,27-tetramethyl-11,28-dioxa-4-azatricyclo[22.3.1.0⁴,⁹]octacos-18-ene-2,3,10-trione; (10)

17-Ethyl-1,14,16-trihydroxy-12-[2'-(4''-hydroxy-3''-methoxycyclohexyl)-1'-methylvinyl]-23,25-dimethoxy-16-furan-2-yl-13,19,21,27-tetramethyl-11,28-dioxa-4-azatricyclo[2-2.3.1.0⁴,⁹]octacos-18-ene-2,3,10-trione; (11)

17-Ethyl-14-hydroxy-12-[2'-(4''-hydroxy-3''-methoxycyclohexyl)-1'-methylvinyl]-23,25-dimethoxy-13,19,21,    -27-tetramethyl-11,28-dioxa-4-azatricyclo[22.3.1.0⁴,⁹]-octacos-1,18-diene-2,3,10,16-tetraone; (12)

17-Ethyl-14-hydroxy-12-[2'-(4''-hydroxy-3''-methoxycyclohexyl)-1'-methylvinyl]-23,25-dimethoxy-13,19,21,    27-tetramethyl-11,28-dioxa-4-azatricyclo[22.3.1.0⁴,⁹]-octacos-18-ene-2,3,10,16-tetraone; (13)

17-Ethyl-14-hydroxy-12-[2'-(4''-hydroxy-3''-methoxycyclohexyl)-1'-methylvinyl]-23,25-dimethoxy-13,19,21, epi-27-tetramethyl-11,28-dioxa-4-azatricyclo-[22.3.1.0⁴,⁹]octacos-18-ene-2,3,10,16-tetraone (14).

B. Preparation of Compounds Within the Scope of the Present Invention

The starting materials for the preparation of the compounds of this invention are represented by Formula II:

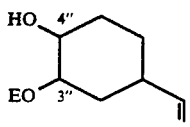

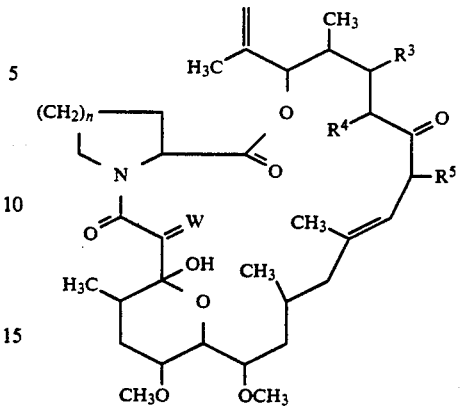

wherein:
E is hydrogen or methyl;
W is O or (H, OH);
$R^3$ is hydrogen, hydroxy, or $C_{1-6}$ alkoxy;
$R^4$ is hydrogen, or $R^3$ and $R^4$ taken together form a double bond;
$R^5$ is methyl, ethyl, propyl or allyl; and
n is 1 or 2.

The production and characterization of compounds of Formula II is well known in the literature (see U.S. Pat. No. 4,894,366 issued Jan. 16, 1990; U.S. Pat. No. 4,929,611 issued May 29, 1990; U.S. Pat. No. 3,244,592 issued Apr. 15, 1966; EPO Publication No. 0,323,042,; EPO Publication No. 0,356,399; PBJ Disclosure 63-17884; *J. Am. Chem. Soc.*, 1987, 109, 5031; *J. Antibiotics*, 1987, 40, 1249; *J. Antibiotics*, 1988, 41 (11), 1592; and *J. Antibiotics*, 1992, 45 (1), 118). Both biological fermentation and synthetic processes may be found. A synthetic route to compounds of Formula II can involve modifications of a route described in *J. Am. Chem. Soc.*, 1989, 111, 1157.

Biological fermentation followed by synthetic modification is presently favored in the art as the method to produce compounds of Formula II. Organisms belonging to the genus Streptomyces such as *Streptomyces tsukubaensis*, No. 9993 and *Streptomyces hygroscopicus*, var. *ascomycetis*, No. 14891 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where E is methyl, W is O, $R^3$ is hydroxyl, $R^4$ is hydrogen, $R^5$ is allyl and n is 2; (B) where E is methyl, W is O, $R^3$ is hydroxyl, $R^4$ is hydrogen, $R^5$ is ethyl and n is 2; (C) where E is methyl, W is O, $R^3$ is hydroxyl, $R^4$ is hydrogen, $R^5$ is methyl and n is 2; and (D) where E is methyl W is O, $R^3$ is hydroxyl, $R^4$ is hydrogen, $R^5$ is allyl and n is 1.

A lyophilized sample of the isolated *Streptomyces tsukubaensis*, No. 9993 was deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposit date: Oct. 5th, 1984), and then converted to Budapest Treaty route of the same depository on Oct. 19, 1985 under the new deposit number of FERM BP-927.

Using the four compounds produced in fermentation above, the remaining compounds of Formula II may be easily produced. The allyl of $R^5$ may be conveniently reduced to propyl by well known methods, for example as described in U.S. Pat. No. 4,894,366. The hydroxy of $R^3$ may be protected by well known methods, for example as disclosed in EPO Publication No. 0,323,042. Likewise, the hydroxyl at C-4" may also be protected. In addition, the hydroxy of $R^3$ may be reduced to a hydrogen or eliminated to form a double bond with $R^4$ (by methods disclosed in U.S. Pat. No. 4,894,366, EPO Publication No. 0,323,042 or EPO Publication No. 0,413,532). The carbonyl of W may be reduced to the alcohol by methods disclosed in EPO Publication No. 0,323,042 or by methods disclosed in EPO Publication No. 0,445,975. The hydroxy of $R^8$ may be introduced by methods disclosed in EPO Publication No. 0,463,690.

The methyl of E as produced may be replaced with hydrogen or demethylated and subsequently protected as desired, if necessary. This demethylation of compounds wherein E is methyl may be carried out in a fermentation reaction using the compounds of Formula II as a feedstock. For instance, compound A named under Formula II above may be demethylated at E above by using the microorganism Actinomycetales ATCC No. 53771 (described in U.S. Pat. No. 4,981,792) or by using the microorganism *Streptomyces tsukubaensis*, No. 9993 (described in EPO Publication No. 0,353,678). Similarly, compound B named under Formula II above may be demethylated at E above using the microorganism Actinoplanacete sp. ATCC No. 53771 (described in EPO Publication No. 0,349,061). In addition the compound of Formula II wherein E is H, W is O, $R^3$ is hydroxy, $R^4$ is hydrogen, $R^5$ is ethyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No.

Similarly, the compound of Formula II wherein E is hydrogen, W is O, $R^3$ is hydroxy, $R^4$ is hydrogen, $R^5$ is methyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (EPO Publication No. 0,388,153). The hydroxy of C-3" may be protected by methods similar to those known for the protection of the hydroxyl groups of $R^3$ and/or C-4", for example as disclosed in U.S. Pat. No. 4,894,366.

Suitable protecting groups for hydroxyl include those groups well known in the art such as: methylthiomethyl, ethylthiomethyl; trisubstituted silyl such as trimethylsilyl, triethylsilyl, tributylsilyl, tri-i-propylsilyl, t-butyldimethylsilyl, tri-t-butylsilyl, methyldiphenylsilyl, ethyldiphenylsilyl, t-butyldiphenylsilyl, and the like; acyl such as acetyl, pivaloyl benzoyl, 4-methoxybenzoyl, 4-nitrobenzoyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in U.S. Pat. No. 4,894,366, dated Jan. 16, 1990 and U.S. Pat. No. 4,929,611, issued May 29, 1990.

The novel processes for preparing the novel compounds of the present invention are illustrated as follows, wherein $R^1$, $R^2$, $R^3$, $R^5$, $R^6$, $R^7$, $R^8$, $R^9$, $R^{10}$, $R^{11}$, E, W and n are as defined above unless otherwise indicated. It will be readily apparent to one of ordinary skill in the art reviewing the synthetic route depicted below that other compounds within Formula I can be synthesized by substitution of appropriate reactants and agents in the synthesis shown below.

14891) (as described in EPO Publication No. 0,388,152).

REACTION SCHEME A

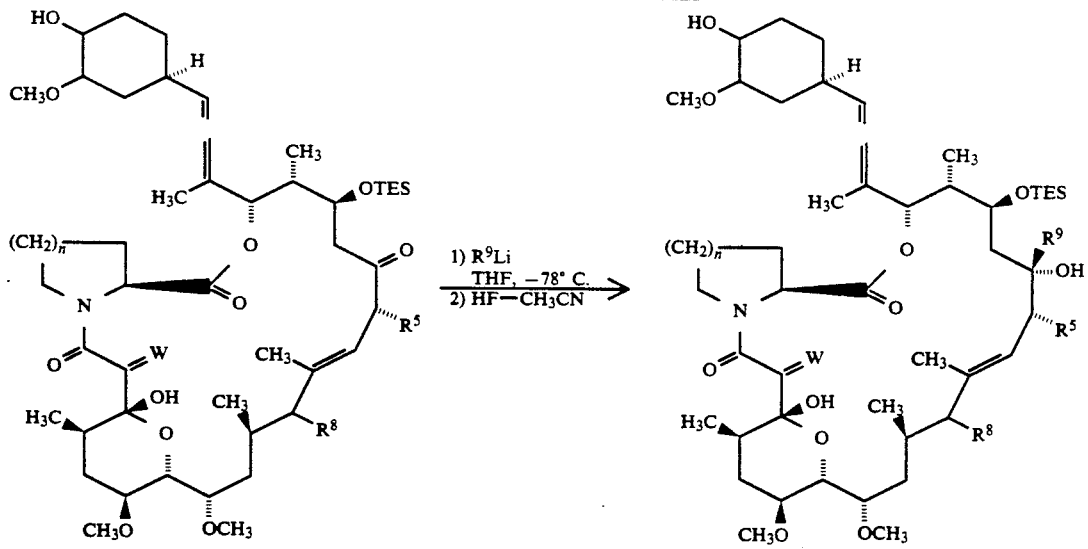

REACTION SCHEME B

-continued
REACTION SCHEME B
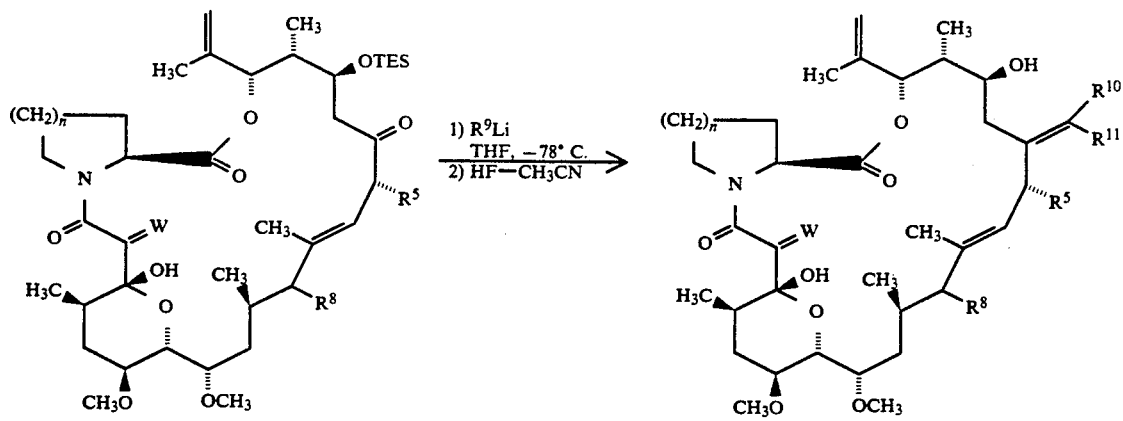
REACTION SCHEME C
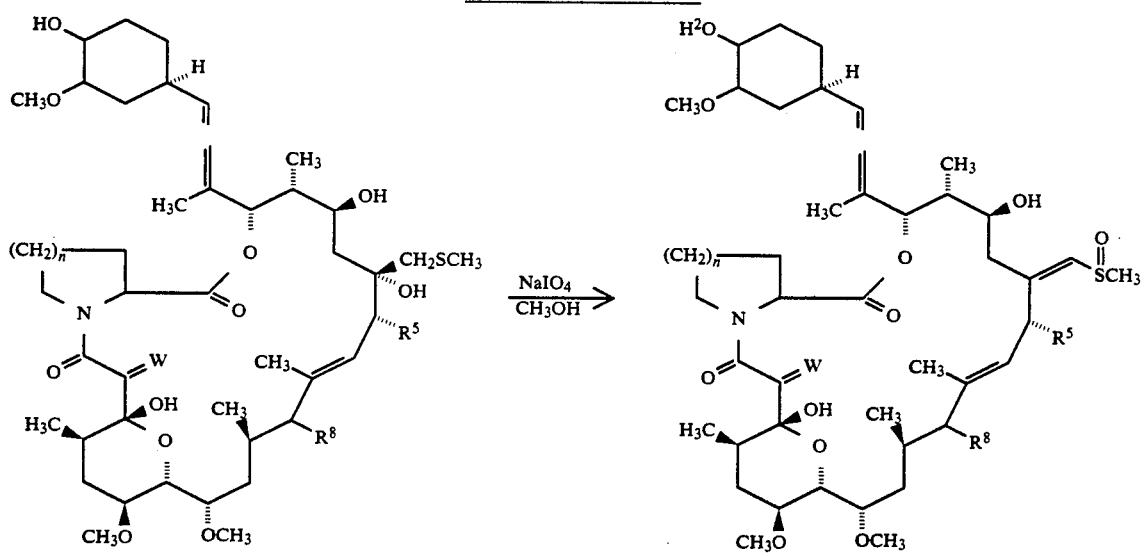
REACTION SCHEME D
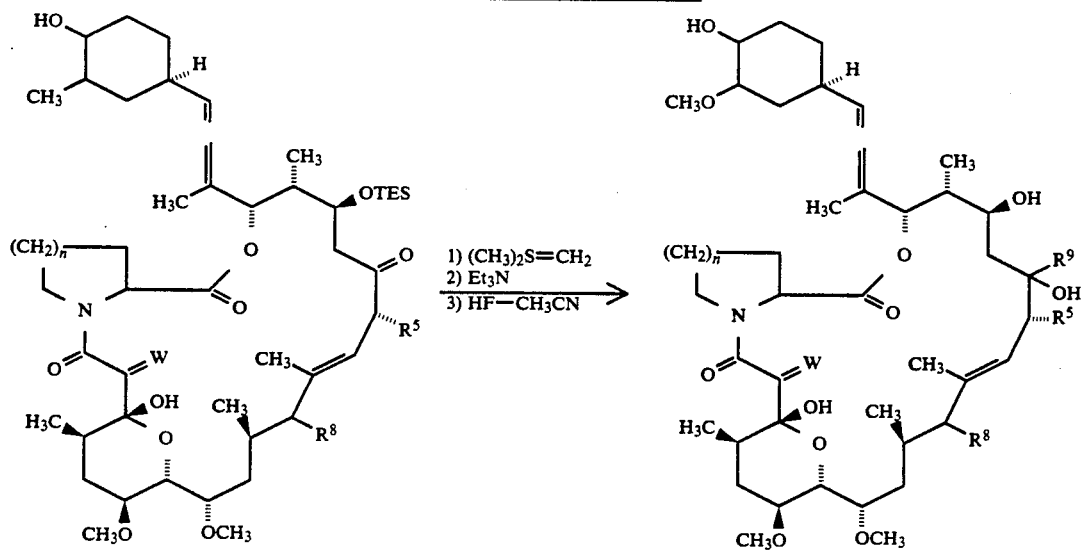

REACTION SCHEME E
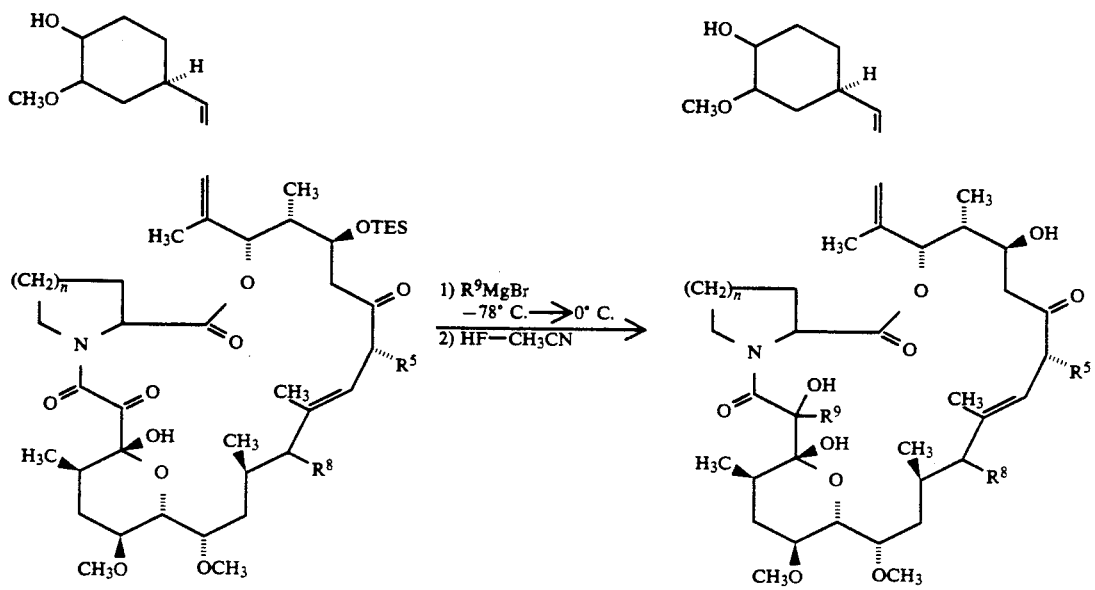
REACTION SCHEME F
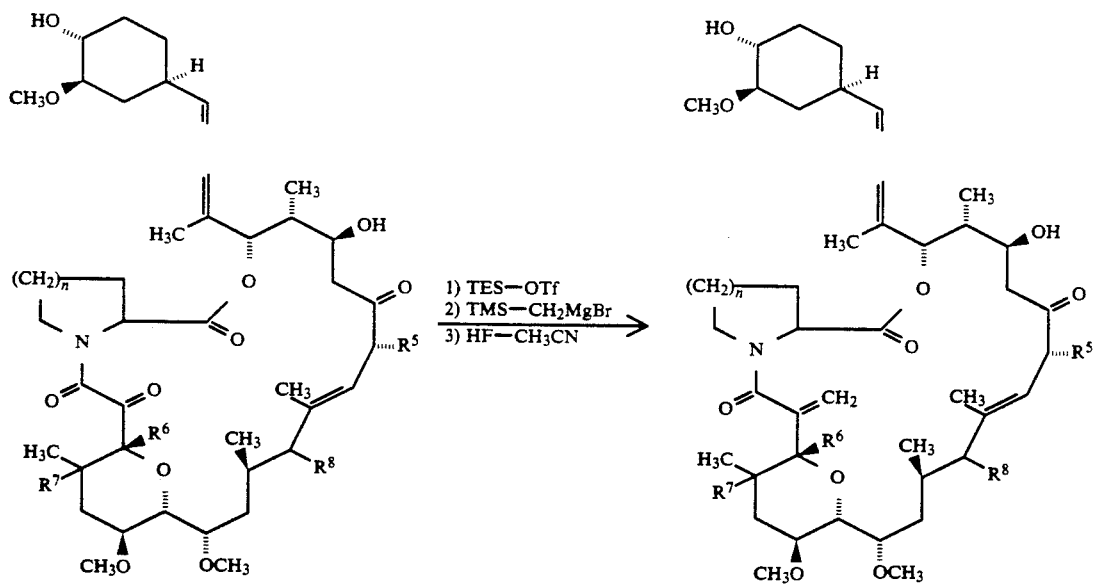
REACTION SCHEME G

-continued
REACTION SCHEME G

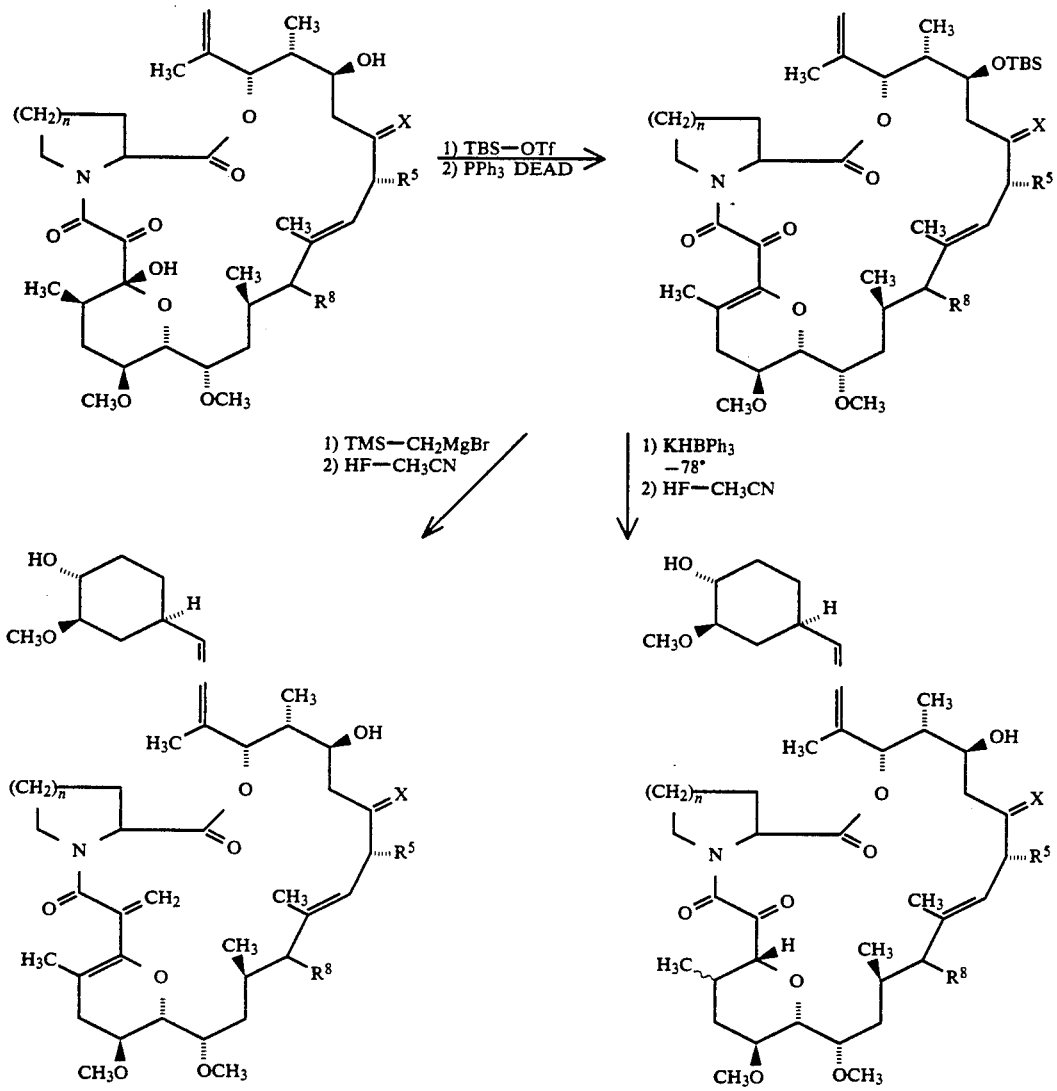

Reaction Scheme A

As shown in Reaction Scheme A, when the reaction mixture is maintained at low temperature (−78° C.) throughout the reaction sequence and the nucleophile contains a non-chelating carbanion [e.g. a lithium carbanion (either alkyl or aryl], the nucleophile adds selectively to the 22-carbonyl group of a 24,32-protected analog. When the nucleophile ($R^9Li$) is a primary carbanion ($RCH_2Li$ or $ArLi$), the addition results in a 22-alkyl-22-hydroxy product [Examples 3, 4 (methyl), 5 (butyl), 10 (methylthiomethyl), 16 (phenyl), 17 (furan2-yl)]. These anions tend to add to the less-hindered face of the carbonyl and form the α-hydroxy group as indicated in the Scheme.

Reaction Scheme B

As shown in Reaction Scheme B, when the nucleophile ($R^9Li$) is a secondary carbanion ($R^{10}R^{11}CHLi$) or when the nucleophile is an α-silyl-α-lithio carbanion (Examples 6,7,8,9), the addition is followed by elimination, resulting in an olefination sequence ($R^{10}R^{11}CHLi$) and affording a 22-alkylidene product.

Reaction Scheme C

As shown in Reaction Scheme C, when the nucleophile contains a sulfur heteroatom, that sulfur may be oxidized to afford the corresponding sulfoxide as a mixture of S-stereoisomers (Example 11). When the 22-hydroxy group is β to the newly formed sulfoxide, that hydroxy group may eliminate, forming the corresponding vinyl sulfone (Example 12).

Reaction Scheme D

As shown in Reaction Scheme D, when the nucleophile is a sulfur ylid, it adds to either face of the 22-carbonyl, forming a mixture of stereoisomers at that position (Example 13). The new sulfonium species may be dealkylated to afford the corresponding 22 alkyl-22-hydroxy analogs with either configuration at that position (Examples 14 and 15).

Reaction Scheme E

As shown in Reaction Scheme E, when the reaction is initiated at low temperature (−78° C.) but allowed to warm to 0° C. and when a chelating carbanion (either alkyl or aryl) is used as the nucleophile, the nucleophile will preferentially add to the 9-carbonyl group of a 24,32-protected analog (Examples 19, 20).

Reaction Scheme F

As shown in Reaction Scheme F, when the carbanion contains an α-silyl substituent, the addition is followed by elimination, affording a 9-alkylidene product (Example 18). This 9-alkylidene may rearrange to afford the intramolecular Michael adduct (Example 21).

Reaction Scheme G

As shown in Reaction Scheme G, this Michael rearrangement might be prevented by utilizing the 10-deoxy analog or the $\delta^{10,11}$ analogs as substrates (Examples 22, 23, and 24).

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereoisomer(s) of starting and object compounds due to asymmetric carbon atom(s) or double bond(s) of the object compounds of Formula I may occasionally be transformed into the other stereo isomer(s), and such cases are also included within the scope of the present invention.

In the present invention, compounds with asymmetric centers may occur as racemates, as diastereomeric mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (*J. Am. Chem. Soc.* 1989, 111, 1157; *J. Am. Chem. Soc.* 1990, 112, 2998; *J. Org. Chem.* 1990, 55, 2786; *J. Am. Chem. Soc.* 1990, 112, 5583. *Tetrahedron Lett.* 1988, 29, 277; *Tetrahedron Lett.* 1988, 29, 281; *Tetrahedron Lett.* 1988, 29, 3895; *J. Org. Chem.* 1988, 53, 4643; *Tetrahedron Lett.* 1988, 29, 4245; *Tetrahedron Lett.* 1988, 29, 4481; *J. Org. Chem.* 1989, 54, 9; *J. Org. Chem.* 1989, 54, 11; *J. Org. Chem.* 1989, 54, 12; *J. Org. Chem.* 1989, 54, 15; *J. Org. Chem.* 1989, 54, 17; *Tetrahedron Lett.* 1989, 30, 919; *Tetrahedron Lett.* 1989, 30, 1037; *J. Org. Chem.* 1989, 54, 2785; *J. Org. Chem.* 1989, 54, 4267; *Tetrahedron Lett.* 1989, 30, 5235; *Tetrahedron Lett.* 1989, 30, 6611; *Tetrahedron Lett.* 1989, 30, 6963; *Synlett* 1990, 38; *J. Org. Chem.* 1990, 55, 2284; *J. Org. Chem.* 1990, 55, 2771; *J. Org. Chem.* 1990, 55, 2776; *Tetrahedron Lett.* 1990, 31, 1439; *Tetrahedron Lett.* 1990, 31, 1443; *Tetrahedron Lett.* 1990, 31, 3007; *Tetrahedron Lett.* 1990, 31, 3283, 3287).

The compounds of the present invention are capable of forming salts with various inorganic and organic acids and bases and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl suflfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

C. Utility of the Compounds Within the Scope of the Invention

The compounds of Formula I may be employed as immunosuppressants or antimicrobial compounds by methods and in dosages known in the prior art for compounds of Formula II. These compounds possess pharmacological activity such as immunosuppressive activity, antimicrobial activity, and the like, and therefore are useful for the treatment and prevention of the resistance to transplantation or transplantation rejection of organs or tissues such as heart, kidney, liver, duodenum, small-bowel, medulla ossium, skin, pancreatic islet-cell, etc., graft-versus-host diseases by medulla ossium transplantation, autoimmune diseases such as rheumatoid arthritis, systemic lupus erythematosis, Hashimoto's thyroiditis, multiple sclerosis, myasthenia gravis, type I diabetes, uveitis, allergic encephalomyelitis, glomerulonephritis, etc., and infectious diseases caused by pathogenic microorganisms.

The compounds of Formula I are also useful for treating inflammatory and hyperproliferative skin diseases and cutaneous manifestations of immunologically-mediated illnesses such as: psoriasis, atopical dermatitiis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias or Alopecia areata. More particularly, the compounds of Formula I are useful in hair revitalizing, such as in the treatment of male pattern alopecia or alopecia senilis, by providing epilation prevention, hair germination, and/or a promotion of hair generation and hair growth.

The compounds of Formula I are further useful for treating reversible obstructive airways disease, including conditions such as asthma, including bronchial asthma, allergic asthma, intrinsic asthma, extrinsic asthma and dust asthma, particularly chronic or inveterate asthma (for example late asthma and airway hyperreponsiveness), bronchitis and the like. The compounds of Formula I may also be useful for treating hepatic injury associated with ischemia.

The compounds of Formula I are also useful for treating multidrug resistance of tumor cells, (i.e. enhancing the activity and/or sensitivity of chemotherapeutic agents), preventing or treating inflammation of mucosa or blood vessels, LTB$_4$-mediated diseases, gastric ulcers, vascular damage caused by ischemic diseases and thrombosis, ischemic bowel disease, inflammatory bowel disease (e.g., Crohn's disease and ulcerative colitis) necrotizing enterocolitis, or intestinal lesions associated with thermal burns, cytomegalovirus infection, particularly HCMV infection, idiopathic thrombocytopenic purpura and Basedow's disease.

Further, the compounds of Formula I are also useful for treating or preventing renal diseases selected from interstitial nephritis, Goodpasture's syndrome, hemolytic-uremic syndrome and diabetic nephropathy; nervous diseases selected from multiple myositis, Guillain-Barre syndrome, Meniere's disease and radiculopathy; endocrine diseases selected from hyperthyroidism; hematic diseases selected from pure red cell aplasia, aplastic anemia, hypoplastic anemia, autoimmune hemolytic anemia, agranulocytosis and anerythroplasia; bone diseases such as osteoporosis; respiratory diseases selected from sarcoidosis, fibroid lung and idiopathic interstitial pneumonia; eye diseases selected from herpetic keratitis, conical cornea, dystrophia epithelialis corneae, corneal leukmas, ocular pemphigus, Mooren's ulcer, scleritis and Grave's ophthalmopathy; skin diseases selected from dermatomyositis, leukoderma vulgaris, ichthyosis vulgaris, photoallergic sensitivity and cutaneous T cell lymphoma; circulatory diseases selected from arteriosclerosis, aortitis syndrome, polyarteritis nodosa and myocardosis; collagen diseases selected from scleroderma, Wegener's granuloma and Sjogren's syndrome; adiposis; eosinophilic fasciitis; periodontal disease; and muscular dystrophy.

The compounds of Formula I may also act as antagonists of macrocyclic immunosuppressive compounds, including derivatives of 12-(2'-cyclohexyl-1'-methylvinyl)-13,19,21,27-tetramethyl-11,28-dioxa-4-azatricyclo[22.3.1.0$^{4,9}$]octacos-18-ene, and so be useful in the treatment of immunodepression (such as AIDS, cancer, senile dementia, trauma (including wound healing, surgery and shock), chronic bacterial infection and certain central nervous system disorders), overdosages or toxicity of such immunosuppressive compounds, and as an adjunct to the administration of an antigen in vaccination.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semi-solid, or liquid form, and in addition auxiliary, stabilizing, thickening and coloring agents and perfumes may be used. For example, the compounds of Formula I may be utilized with hydroxypropyl methylcellulose essentially as described in U.S. Pat. No. 4,916,138, issued Apr. 10, 1990, or with a surfactant essentially as described in EPO Publication 0,428,169. Oral dosage forms may be prepared essentially as described by T. Hondo, et al., *Transplantation Proceedings*, 1987, XIX, Supp. 6, 17-22. Dosage forms for external application may be prepared essentially as described in EPO Publication 0,423,714. The active object compound is included in the pharmaceutical composition in an amount sufficient to produce the desired effect upon the process or condition of diseases.

For the treatment of these conditions and diseases caused by immunoirregularity a compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For modifying the activity and/or toxicity of FK-506-type immunosuppressants, a compound of Formula I may be administered prior to, in conjunction with or subsequent to the administration of an FK-506-type of a compound.

Dosage levels of the compounds of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 mg per patient per day, assuming a 70 kg patient). In addition, the compounds of the present invention may be administered on an intermittent basis; i.e. at semiweekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally comprise from about 0.01 mg to about 500 mg, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

PREPARATION OF STARTING INTERMEDIATES

17-Ethyl-1-hydroxy-12-[2'-(4'''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone A solution of 500 mg of 17-ethyl-1,14-dihydroxy-12-[2'-(4'''-hydroxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone in 7 ml of benzene was treated with 10 mg of p-toluenesulfonic acid and the solution was heated at 60° C. for two hours. The reaction mixture was quenched into saturated sodium bicarbonate solution and extracted with ethyl acetate. The combined organic layers were washed with water and saturated sodium chloride solution, dried with anhydrous magnesium sulfate and concentrated. The residue was chromatographed on silica gel (66% ethyl acetate: 33% hexane: 1% methanol) to give 350 mg of product. This material was dissolved in 10 ml of ethyl acetate and treated with 15 mg of 5% Rh/C. A balloon containing hydrogen was placed over the reaction mixture and the mixture stirred until the reaction was complete. The mixture was filtered through diatomaceous earth, concentrated and the residue subjected to chromatography (75% $CH_2Cl_2$: 5% MeOH: 20% Hexane) to give 294 mg of product.

17-Ethyl-1-hydroxy-12-[2'-(4",3"-dihydroxyoxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone A solution of 17-ethyl-1,14-dihydroxy-12-[2'-(4"-hydroxy-3"-hydroxycyclohexyl)-1'-methylvinyl]-23,25-dimethoxy-13,19,21,27-tetramethyl-11,28-dioxa-4-azatricyclo-[22.3.1.0⁴,⁹]octacos-18-ene-2,3,10,16-tetraone (210 mg) and a catalytic amount of p-toluenesulfonic acid in 40 ml of benzene was refluxed for 4 hours under a nitrogen atmosphere. The solvent was removed under reduced pressure and the dark residue was purified by chromatography (silica gel, 7% i-propanol/$CH_2Cl_2$) to give 17-ethyl-1-hydroxy-12-[2'-(4"-hydroxy-3"-isopropyloxycyclohexyl)-1'-methylvinyl]-23,25-dimethoxy-13,19,21,-27-tetramethyl-11,28-dioxa-4-azatricyclo-[22.3.1.0⁴,⁹]octacos-14,18-diene-2,3,10,16-tetraone (180 mg) as a white solid. This material was dissolved in ethanol (20 ml) and treated with 5% Rh/C (40 mg). Hydrogen was introduced via balloon for 30 min. and the mixture was filtered through celite. Removal of solvent followed by chromatography (silica gel) gave 172 mg of the title compound. Mass, ¹H and ¹³C NMR data were consistant with the title structure.

17-Ethyl-1-hydroxy-12-[2'-(4"-triisopropylsilyloxy-3"-methoxycyclohexyl)-1'-methylvinyl]-14-triisopropylsilyloxy-23,25-dimethoxy-13,19,21,27-tetramethyl-11,28-dioxa-4-azatricyclo-[22.3.1.0⁴,⁹]octacos-18-ene-2,3,10,16-tetraone To a cooled solution (0° C.) of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone (120 mg) in dry methylene chloride (15 ml) was added 2,6-lutidine (64.3 mg) followed by triisopropylsilyl trifluoromethanesulfonate (184 mg). Reaction temperature was raised to r.t. and stirred overnight under nitrogen atmosphere. The reaction was quenched with 10 ml of water and extracted with ethyl acetate. Organic layer was washed (water, sat'd NaHCO₃, sat'd NaCl) and dried (anhydrous MgSO₄). Removal of solvent followed by chromatography on silica gel (70% hexane/ethyl acetate) gave 150 mg of product. MASS: (FAB) 1110 (M⁺ +Li).

17-Ethyl-1-hydroxy-12-[2'-(4"-hydroxy-3"-methoxycyclohexyl)-1'-methylvinyl]-14-triisopropylsilyloxy-23,25-dimethoxy-13,19,21,27-tetramethyl-11,28-dioxa-4-azatricyclo[22.3.1.0⁴,⁹]-octacos-18-ene-2,3,10,16-tetraone The title compound from the previous preparation (680 mg) was dissolved in methylene chloride (45 ml) and 10% solution of p-toluenesulfonic acid in methanol (45 ml) was added with stirring. The mixture was stirred at room temperature and the progress was followed by tlc analysis. After 4 hr, reaction was quenched with sat'd sodium bicarbonate and extracted with ethyl acetate three times. Normal work-up and removal of solvent followed by purification on silica gel column (80% ethyl acetate/hexane) gave 560 mg of the product (2a) as a white solid. MASS: (FAB) 954 (M⁺ +Li).

17-Ethyl-1-hydroxy-12-[2'-(4"-t-butyldimethylsilyloxy-3"-methoxycyclohexyl)-1'-methylvinyl]-14-t-butyl-dimethylsilyloxy-23,25-dimethoxy-13,19,21,27-tetramethyl-11,28-dioxa-4-azatri-cyclo[22.3.1.0⁴,⁹]octacos-18-ene-2,3,10,16-tetraone To a cooled solution (0° C.) of 17-ethyl-1,14-dihydroxy-12-[2'-(4"-hydroxy-3"-methoxycyclohexyl)-1'-methylvinyl]-23,25-dimethoxy-13,19,21,27-tetra-methyl-11,28-dioxa-4-azatricyclo[22.3.1.0⁴,⁹[octacos-18-ene-2,3,10,16-tetraone (1a) (395 mg) in dry methylene chloride (15 ml) was added 2,6-lutidine (160 mg) followed by t-butyldimethylsilyl triflouromethanesulfonate (250 mg). Reaction temperature was raised to r.t. and stirred under nitrogen atmosphere. After 6 hr, the reaction was quenched with 10 ml of water and extracted with ethyl acetate. Organic layer was washed (water, saturated NaHCO₃, saturated NaCl) and dried (anhydrous MgSO₄). Removal of solvent under reduced pressure gave 500 mg of crude product. MASS: (FAB) 1026 (M⁺ +Li).

17-Ethyl-1-hydroxy-12-[2'-(4"-hydroxy-3"-methoxycyclohexyl)-1'-methylvinyl]-14-t-butyldimethylsilyloxy-23,25-dimethoxy-13,19,21,27-tetramethyl-11,28-dioxa-4-azatricyclo[22.3.1.0⁴,⁹]octacos-18-ene-2,3,10,16-tetraone The product from the previous example (500 mg) was dissolved in acetonitrile (20 ml) and 100 ml of hydrogen fluoride (48%) was added. Reaction was stirred for 20 minutes at room temperature, quenched with saturated sodium bicarbonate, then extracted with ethyl acetate. Removal of solvent in vacuo followed by chromatography on silica gel (80% ethyl acetate/hexane) gave 300 mg of product (Mass, ¹H and ¹³C NMR data consistent with the title compound.

17-Ethyl-1-hydroxy-12-[2'-(4"-(tert-butyldimethylsiloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone To a solution of 17-ethyl-1-hydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.04,9]octacos-18-ene-2,3,10,16-tetraone (3.01 g) in dry methylene chloride (70 ml) was added an excess of imidazole (809 mg) followed by tert-butyldimethylsilyl chloride (716 mg). After 3 days of stirring at room temperature, the mixture was diluted with ethyl acetate which in turn was washed with 1N HCl, saturated sodium bicarbonate and brine, dried over magnesium sulfate and purified by flash chromatography (ethyl acetae:hexane (1:3)) to give the title compound (941 mg). $^1$H NMR consistent with the desired structure.

17-Ethyl-1-hydroxy-12-[2'-(4"-(tert-butyldimet hylsilyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4"-hydroxy-3"-methoxycyclohexyl)-1'-methylvinyl]-23,25-dimethoxy-13,19,21,-27-tetramethyl-11,28-dioxa-4-azatricyclo[22.3.1.0$^{4,9}$]octacos-18-ene-2,3,10,16-tetraone (200 mg) in dry methylene chloride (3 ml) was added an excess of 2,6-lutidine (45 µl) and the mixture was stirred at room temperature. After 10 minutes, tert-butyldimethylsilyl trifluoromethanesulfonate (64 µl) was added by syringe. After 15 minutes the reaction mixture was diluted with ethyl acetate, extracted from saturated bicarbonate, washed with brine and the organic phase dried over magnesium sulfate. Removal of solvent in vacuo and flash chromatography on silica gel (ethyl acetate:hexane (1:2)+1% methanol) gave the title compound (235 mg).

($^1$H NMR consistent with the desired structure).

17-Ethyl-1,20-dihydroxy-12-[2'-(4"-tert-buty ldimethylsilyloxy)-3"-methoxycyclohexyl)-4"'1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1-hydroxy-12-[2'-(4"-(tert-butyldimethylsilyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (235 mg) in 95% ethanol (2.2 ml) was added 53 µl of pyridine followed by selenium dioxide (58 mg). The flask was fitted with a water condenser and heated to 70° C. on a mantle. After 20 hours the mixture was cooled to room temperature filtered through diatomaceous earth and the filtrate poured into a saturated sodium bicarbonate solution. This was extracted with ethyl acetate, washed with brine and dried over magnesium sulfate. The solution was concentrated and purified by flash chromatography on silica gel (ethyl acetate:hexane (1:2)+1% methanol) to give the title compound (89 mg).

($^1$H NMR consistent with the desired structure).

17-Ethyl-20-fluoro-1-hydroxy-12-[2'-(4"-(tert-b utyldimethylsiloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10.16-tetraone A solution of 17-ethyl-20-dihydroxy-12-[2'-(4"-(tert-butyldimethylsiloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10.16-tetraone (30.5 mg) in methylene chloride (0.5 ml) was cooled to −78° C. in a dry ice/isopropanol bath. To this stirred solution, diethylaminosulfur trifluoride (4.5 µl) was added. After 3 minutes, saturated sodium bicarbonate (500 µl) was added followed by ethyl acetate (2 ml) and the mixture was warmed to room temperature. Extraction from ethyl acetate, drying over magnesium sulfate and purification by flash chromatography on silica gel (ethyl acetate:hexane (1:2)+1% MeOH) gave the title compound (22 mg).

($^1$H NMR consistent with the desired structure).

17-Ethyl-1,20-dihydroxy-12-[2'-(4"-(hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10.16-tetraone To a solution of 17-ethyl-1,20-dihydroxy-12-[2'-(4"-(tert-butyldimethylsiloxy)-3"-methoxycyclohexyl)-1'-methylvinyl]23,25-dimethoxy-13,19,21,27-tetramethyl-11,28-dioxa-4-azatricyclo[22.3.1.0$^{4,9}$]-octacos-18-ene-2,3,10.16-tetraone (7 mg) in acetonitrile (0.3 ml) was added a solution of 2% hydrogen fluoride in aqueous acetonitrile (100 µl), and the mixture stirred at room temperature. After 28 hours the solution was diluted with ethyl acetate, extracted with saturated sodium bicarbonate and the organic phase dried by passage through a magnesium sulfate column. Purification of the concentrate by flash chromatography on silica gel (ethyl acetate:hexane (2:1)+1% methanol) gave the title compound.

17-Ethyl-20-fluoro-1-hydroxy-12-[2'-(4"-(hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10.16-tetraone To a solution of 17-ethyl-20-fluoro-1-hydroxy-12-[2'-(4"-(tert-butyld imethylsiloxy)-3"-methoxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10.16-tetraone (7 mg) in acetonitrile (0.3 ml) was added a solution of 2% hydrogen fluoride in aqueous acetonitrile (100 µl), and the mixture stirred at room temperature. After 2 hours the solution was diluted with ethyl acetate, extracted with saturated sodium bicarbonate and the organic phase dried by passage through a magnesium sulfate column. Purification of the concentrate by flash chromatography on silica gel (ethyl acetate:hexane (1:1)+1% methanol) gave the title compound. MASS: (FAB) 816 (M+Na).

partial $^{13}$C NMR δ: 211.5 (C-16); 196.1 (2) 169.3 (10); 165.0 (3); 138.1 (C-19); 135.8 (C-1'); 121.0 (C-18' major); 84.1 (C-3"); 43.1 (C-15); 26.0 (C-21).

17-Ethyl-1,14,20-trihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Alternate Route To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (5.15 gm, 0.065 mol) in glacial acetic acid (500 ml) at room temperature, was added a solution of selenium dioxide (9.27 gm, 0.083 mol) in H$_2$O (90 ml). The reaction mixture was stirred at room temperature for 41 hours whereupon, it was poured into a stirred mixture of H$_2$O (3 L) and celite. After stirring for 15 minutes, the mixture was filtered through a pad of celite and extracted with diethyl ether (1×2 L, 2×1 L). The organic fractions were washed with saturated sodium bicarbonate and brine, dried over magnesium sulfate, filtrated and evaporated in vacuo. The product was purified by chromatography (silica, acetone:hexanes 2:5) to give the title compound MASS and $^1$H NMR were consistent with the structure.

EXAMPLE 1

17-Ethyl-1-hydroxy-12-[2'-(4"-t-butyldimethylsilyloxy-3"-methoxycyclohexyl)-1'-methylvinyl]-14-t-butyl-dimethylsilyloxy-23,25-dimethoxy-13,19,21,27-tetramethyl-11,28-dioxa-4-azatri-cyclo[22.3.1.0$^{4,9}$]octacos-18-ene-2,3,10,16-tetraone To a cooled solution (0° C.) of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (1a) (4.00, 5 mmole) in dry methylene chloride (50 ml) was added 2,6-lutidine (4 mL, 33 mmole) followed by t-butyldimethylsilyl trifluoromethanesulfonate (5 mL, 21 mmole). Reaction temperature was raised to r.t. and stirred under nitrogen atmosphere. After 2 hr, the reaction was quenched with 10 ml of methanol and partitioned between ether and water. The ether layer was washed sequentially with 2 portions of 2M H$_2$SO$_4$, brine, NaHCO$_3$, and brine, then dried over MgSO$_4$. Removal of solvent under reduced pressure gave 5.4 g of crude product. MASS SPECTRUM (FAB) m/e 1026(M+Li).

EXAMPLE 2

17-Ethyl-1-hydroxy-12-[2'-(4"-triethylsilyloxy-3"-methoxycyclohexyl)-1'-methylvinyl]-14-triethylsilyloxy-23,25-dimethoxy-13,19,21,27-tetramethyl-11,28-dioxa-4-azatri-cyclo[22.3.1.0$^{4,9}$]octacos-18-ene-2,3,10,16-tetraone To a cooled solution (0° C.) of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (4.00, 5 mmole) in dry methylene chloride (50 ml) was added 2,6-lutidine (4 mL, 33 mmole) followed by triethylsilyl trifluoromethanesulfonate (5 mL, 22 mmole). Reaction temperature was raised to r.t. and stirred under nitrogen atmosphere. After 1 hr, the reaction was quenched with 10 ml of methanol and partitioned between ether and water. The ether layer was washed sequentially with 2 portions of 2M H$_2$SO$_4$, brine, NaHCO$_3$, and brine, then dried over MgSO$_4$. Removal of solvent under reduced pressure gave 5.3 g of crude product. MASS SPECTRUM (FAB) m/e 1026(M+Li).

EXAMPLE 3

17-Ethyl-1,14,16-trihydroxy-12-[2'-(4"-hydroxy-3"-methoxycyclohexyl)-1'-methylvinyl]-23,25-dimethoxy-16-methyl-13,19,21,27-tetramethyl-11,28-dioxa-4-azatricyclo[22.3.1.0$^{4,9}$]octacos-18-ene-2,3,10-trione

Step 1:

17-Ethyl-14-t-butyldimethylsilyloxy-1,16-dihydroxy-12-[2'-(4"-t-butyldimethylsilyloxy-3"-methoxycyclohexyl)-1'-methylvinyl]-23,25-dimethoxy-16-methyl-13,19,21,27-tetramethyl-11,28-dioxa-4-azatricyclo[22.3.1.0$^{4,9}$]octacos-18-ene-2,3,10-trione A solution of 0.101 g (0.1 mmole) of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetrone in 5 mL of dry THF was cooled to 0° C. under nitrogen. Then 1 mL of a 0.5M solution of methyllithium was added dropwise and the solution was stirred at −78° C. for 24 h. The solution was quenched at −78° C. by addition of 0.2 mL of glacial acetic acid and then diluted with 20 mL of ether and partitioned between ether and 1M KHCO$_3$ solution. The ether layer was washed with 1M KHCO$_3$ and brine, dried over MgSO4, and concentrated. The residue was purified by flash chromatography (2×20 cm silica gel) using 20% ethyl acetate-hexane to afford the 0.091 g (88%) of title compound as a colorless oil.

$^1$H NMR (CDCl$_3$, 300 MHz) δ0.02-0.04 (s, 12H), 0.6-1.0 (m, 16H), 0.90 (s, 18H), 1.2 (s, 3H, 16-CH$_3$), 1.3-2.4 (m), 2.9 (m, 2H), 3.2-3.6 (m), 3.8 (s, 1H), 4.05 (m, 1H), 4.25 (m, 1H), 4.39 (d, 1H), 4.78 (d, 1H), 4.95 (m, 2H), 5.25 (d, 1H); $^{13}$C NMR (CDCl$_3$, 75 MHz) δ83.8, 97.5, 128.0, 128.7, 133.4, 136.9, 164.8, 168.9, 195.8; MASS SPECTRUM (FAB) 1042(M+Li).

Step 2:

17-Ethyl-1,14,16-trihydroxy-12-[2'-(4"-hydroxy-3"-methoxycyclohexyl)-1'-methylvinyl]-23,25-dimethoxy-16-methyl-13,19,21,27-tetramethyl-11,28-dioxa-4-azatricyclo[22.3.1.0$^{4,9}$]octacos-18-ene-2,3,10-trione A solution of 0.086 g (0.082 mmole) of 17-ethyl-14-t-butyldimethylsilyloxy-1,16-dihydroxy-12-[2'-(4"-t-butyldimethylsilyloxy-3"-methoxycyclohexyl)-1'-methylvinyl]-23,25-dimethoxy-16-methyl-13,19,21,27-tetramethyl-11,28-dioxa-4-azatricyclo[22.3.1.0$^{4,9}$]octacos-18-ene-2,3,10-trione in 2 mL of a solution of 1:9 48% aqueous HF-acetonitrile was stirred at room temperature for 8 h. The reaction was quenched by addition of 2 mL of ethoxytrimethylsilane and the solution was concentrated to dryness under vacuum. The residue was purified by flash chromatography (2×20 cm silica gel) using 25% acetone-hexane to afford 0.051 g (77%) of the title compound as a white solid.

$^1$H NMR (CDCl$_3$, 300 MHz) δ0.7-1.1 (m, 16H), 1.22 (s, 3H, 16CH$_3$), 1.25-2.5 (m), 2.71 (m, 1H), 2.90 (t, 1H), 2.95 (m, 1H), 3.2-3.6 (m), 3.76 (s, 1H), 4.05 (m, 1H), 4.29 (m, 1H), 4.43 (d, 1H), 4.80 (d, 1H), 4.95 (m, 2HO, 5.24 (m, 1H); $^{13}$C NMR (CDCl$_3$, 300 MHz) δ84.1, 97.7, 127.8, 128.2, 133.6, 136.9, 164.9, 168.6, 195.9; MASS SPECTRUM (FAB) 814 (M+Li).

EXAMPLE 4

17-Ethyl-1,14,16-trihydroxy-12-[2'-(4"-hydroxy-3"-methoxycyclohexyl)-1'-methylvinyl]-23,25-dimethoxy-16-methyl-13,19,21,27-tetramethyl-11,28-dioxa-4-azatricyclo[22.3.1.0$^{4,9}$]octacos-18-ene-2,3,10-trione A solution of 0.101 g (0.1 mmole) of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetrone in 5 mL of dry THF was cooled to 0° C. under nitrogen. Then 1 mL of a 0.5M solution of methyllithium was added dropwise and the solution was stirred at −78° C. for 24 h. The solution was quenched at −78° C. by addition of 0.2 mL of glacial acetic acid and then diluted with 20 mL of ether and partitioned between ether and 1M KHCO$_3$ solution. The ether layer was washed with 1M KHCO$_3$ and brine, dried over MgSO4, and concentrated. The residue was dissolved in 2 mL of 1:9 48% aqueous HF-acetonitrile was stirred at room temperature for 8 h. The reaction was quenched by addition of 2 mL of ethoxytrimethylsilane and the solution was concentrated to dryness under vacuum. The residue was purified by flash chromatography (2×20 cm silica gel)

using 25% acetone-hexane to afford 0.053 g (68%) of the title compound as a white solid.

$^1$H NMR (CDCl$_3$, 300 MHz) δ0.7–1.1 (m, 16H), 1.22 (s, 3H, 16CH$_3$), 1.25–2.5 (m), 2.71 (m, 1H), 2.90 (t, 1H), 2.95 (m, 1H), 3.2–3.6 (m), 3.76 (s, 1H), 4.05 (m, 1H), 4.29 (m, 1H), 4.43 (d, 1H), 4.80 (d, 1H), 4.95 (m, 2H), 5.24 (m, 1H); $^{13}$C NMR (CDCl$_3$, 300 MHz) d 84.1, 97.7, 127.8, 128.2, 133.6, 136.9, 164.9, 168.6, 195.9; MASS SPECTRUM (FAB) 814 (M+Li).

EXAMPLE 5

17-Ethyl-1,14,16-trihydroxy-12-[2'-(4"-hydroxy-3''-methoxycyclohexyl)-1'-methylvinyl]-23,25-dimethoxy-16-butyl-13,19,21,27-tetramethyl-11,28-dioxa-4-azatricyclo[22.3.1.0$^{4,9}$]octacos-18-ene-2,3,10-trione Prepared as in Example 4 except that a 2.0M solution of butyllithium was used in place of methyllithium to afford 0.062 g (72%) of the title compound as a white solid; MASS SPECTRUM (FAB) m/e 856 (M+Li).

EXAMPLE 6

17-Ethyl-1,14-dihydroxy-12-[2'-(4"-hydroxy-3''-methoxycyclohexyl)-1'-methylvinyl]-23,25-dimethoxy-16-butyl-13,19,21,27-tetramethyl-16-methenyl-11,28-dioxa-4-azatricyclo[22.3.1.0$^{4,9}$]octacos-18-ene-2,3,10-trione A solution of 0.201 g (0.2 mmole) of 17-ethyl-1,14-dihydroxy-12-[2'-(4"-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetrone in 5 mL of dry THF was cooled to 0° C. under nitrogen. Then 1 mL of a 0.5M solution of trimethylsilylmethyllithium was added dropwise and the solution was stirred at −78° C. for 24 h. The solution was quenched at −78° C. by addition of 0.2 mL of glacial acetic acid and then diluted with 20 mL of ether and partitioned between ether and 1M KHCO$_3$ solution. The ether layer was washed with 1M KHCO$_3$ and brine, dried over MgSO4, and concentrated. The residue was dissolved in 2 mL of 1:9 48% aqueous HF-acetonitrile was stirred at room temperature for 8 h. The reaction was quenched by addition of 2 mL of ethoxytrimethylsilane and the solution was concentrated to dryness under vacuum. The residue was purified by flash chromatography (2×20 cm silica gel) using 25% acetone-hexane to afford 0.137 g (86%) of the title compound as a white solid.

$^1$H NMR (CDCl$_3$, 300 MHz) δ0.7–1.1 (m, 16H), 1.25–2.5 (m), 2.59 (s, 1H), 2.7–3.1 (m, 3H), 3.2–3.6 (m), 3.63 (d, 1H), 3.76 (s, 1H), 4.35 (d, 1H), 4.45 (d, 1H), 4.80 (d, 1H), 5.95 (m, 3H), 5.16 (s, 1H), 5.29 (m, 1H); $^{13}$C NMR (CDCl$_3$, 300 MHz) d 84.1, 97.7, 117.8, 127.9, 128.2, 133.6, 136.9, 147.4, 164.9, 168.6, 195.9; MASS SPECTRUM (FAB) 796 (M+Li).

EXAMPLE 7

17-Ethyl-1,14-dihydroxy-12-[2'-(4"-hydroxy-3''-methoxycyclohexyl)-1'-methylvinyl]-23,25-dimethoxy-16-butyl-13,19,21,27-tetramethyl-16-(2-butenyl)-11,28-dioxa-4-azatricyclo[22.3.1.0$^{4,9}$]octacos-18-ene-2,3,10-trione Prepared as in Example 4 except that a 2.0M solution of sec-butyllithium was used in place of methyllithium to afford 0.068 g (71%) of the title compound as a white solid; MASS SPECTRUM (FAB) m/e 838 (M+Li).

EXAMPLE 8

17-Ethyl-1,14-dihydroxy-12-[2'-(4"-hydroxy-3''-methoxycyclohexyl)-1'-methylvinyl]-23,25-dimethoxy-16-propenyl-13,19,21,27-tetramethyl-11,28-dioxa-4-azatricyclo[22.3.1.0$^{4,9}$]octacos-18-ene-2,3,10-trione (fast isomer)

Prepared as in Example 6 except that a solution of 1-trimethylsilylpropyllithium was used in place of methyllithium to afford 0.042 g (51%) of the title compound as a white solid; MASS SPECTRUM (FAB) m/e 824 (M+Li).

EXAMPLE 9

17-Ethyl-1,14-dihydroxy-12-[2'-(4"-hydroxy-3''-methoxycyclohexyl)-1'-methylvinyl]-23,25-dimethoxy-16-propenyl-13,19,21,27-tetramethyl-11,28-dioxa-4-azatricyclo[22.3.1.0$^{4,9}$]octacos-18-ene-2,3,10-trione (slow isomer)

Further elution of the column from Example 8 with 25% acetone-hexane afforded 0.032 g (39%) of the title compound as a white solid; MASS SPECTRUM (FAB) m/e 824 (M+Li).

EXAMPLE 10

17-Ethyl-1,14,16-trihydroxy-12-[2'-(4"-hydroxy-3''-methoxycyclohexyl)-1'-methylvinyl]-23,25-dimethoxy-16-(methylthiomethyl)-13,19,21,27-tetramethyl-11,28-dioxa-a-4-azatricyclo[22.3.1.0$^{4,9}$]octacos-18-ene-2,3,10-trione Prepared as in Example 4 except that a solution of methylthiomethyllithium was used in place of methyllithium to afford 0.079 g (92%) of the title compound as a white solid; MASS SPECTRUM (FAB) m/e 860 (M+Li).

EXAMPLE 11

17-Ethyl-1,14,16-trihydroxy-12-[2'-(4"-hydroxy-3''-methoxycyclohexyl)-1'-methylvinyl]-23,25-dimethoxy-16-(methylsulfinylmethyl)-13,19,21,27-tetramethyl-11,28-dioxa-4-azatricyclo[22.3.1.0$^{4,9}$]octacos-18-ene-2,3,10-trione A solution of 0.050 g (0.059 mmole) of 17-ethyl-1,14,16-trihydroxy-12-[2'-(4"-hydroxy-3''-methoxycyclohexyl)-1'-methylvinyl]-23,25-dimethoxy-16-(methylthiomethyl)-13,19,21,27-tetramethyl-11,28-dioxa-4-azatricyclo[22.3.1.0$^{4,9}$]octacos-18-ene-2,3,10-trione in 5 mL of methanol was cooled to 0° C. in an ice bath. Then 2 mL of a 0.5M solution of NaIO$_4$ was added and the mixture was stirred at room temperature for 1 h. The solution was partitioned between ether and water and the ether layer was washed with KHCO$_3$ and brine, then dried over MgSO$_4$ and concentrated. The residue was purified by flash chromatography (2×20 cm silica gel) using 20% acetone-hexane to afford 0.022 g (44%) of the title compound as a white solid; MASS SPECTRUM (FAB) m/e 876 (M+Li).

EXAMPLE 12

17-Ethyl-1,14,16-trihydroxy-12-[2'-(4"-hydroxy-3''-methoxycyclohexyl)-1'-methylvinyl]-23,25-dimethoxy-16-(methylsulfinylmethenyl)-13,19,21,27-tetramethyl-11,28-dioxa-4-azatricyclo[22.3.1.0$^{4,9}$]octacos-18-ene-2,3,10-trione Further elution of the column in Example 10 with 30% acetone-hexane afforded 0.018 g (35%) of the title

EXAMPLE 13

17-Ethyl-16-(triethylsilyloxy) 1,14-dihydroxy-12-[2'-(4"-triethylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10-trione-16-(methyldimethylsulfonium) iodide To a stirred solution of 612 mg trimethylsulfonium iodide (3.0 mmole) in 3.9 mL of THF at 0° C. was added methyllithium (1.4M in ether, 2.1 mL, 2.94 mmole). The mixture was stirred for 1 h at 0° C. To 2 mL of the resultant solution at −78° C. was added 200 mg of 17-ethyl-1-hydroxy-12-[2'-(4"-triethylsilyloxy-3"-methoxycyclohexyl)-1'-methylvinyl]-14-triethylsilyloxy-23,25-dimethoxy-13,19,21,27-tetramethyl-11,28-dioxa-4-azatri-cyclo[22.3.1.0$^{4,9}$]octacos-18-ene-2,3,10,16-tetraone (0.2 mmole) and the mixture was stirred at −78° C. for 2 h. The reaction was quenched with two drops of glacial acetic acid, diluted with ether and washed with sat aq. KHCO$_3$, water and brine. The residue was purified by flash chromatography (2×20 cm silica gel) using 20% ethyl acetate-hexane remove starting material, followed by 5% CH$_3$OH—CH$_2$Cl$_2$ to afford 0.034 g (17%) of the title compound as a white solid; MASS SPECTRUM (FAB) m/e 1096 (M+)

EXAMPLE 14

17-Ethyl-16-triethylsilyloxy-1,14-dihydroxy-12-[2'-(4"-triethylsilyloxy-3"-methoxycyclohexyl)-1'-methylvinyl]-23,25-dimethoxy-16-(methylthiomethyl)-13,19,21,27-tetramethyl-11,28-dioxa-4-azatricyclo[22.3.1.0$^{4,9}$]octacos-18-ene-2,3,10-trione (faster isomer)

Step 1:
17-Ethyl-1,16-dihydroxy-12-[2'-(4"-triethylsilyloxy-3"-methoxycyclohexyl)-1'-methylvinyl]-14-triethylsilyloxy-23,25-dimethoxy-16-(methylthiomethyl)-13,19,21,27-tetramethyl-11,28-dioxa-4-azatricyclo[22.3.1.0$^{4,9}$]octacos-18-ene-2,3,10-trione (faster isomer)

A sample of 34 mg (0.034 mmole) of 17-ethyl-16-(triethylsilyloxy) 1,14-dihydroxy-12-[2'-(4"-triethylsilyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]one-16-(methyldimethylsulfonium) iodide was dissolved in 3 mL of CH$_2$Cl$_2$ and treated with four drops of triethylamine. The solution was concentrated under vacuum and the residue was purified by flash chromatography (1.5 cm×15 cm) using 10% ethyl acetate-hexane to afford 0.12 g (32%) the title compound as a white solid; MASS SPECTRUM (FAB) m/e 1088 (M+Li).

Step 2:
17-Ethyl-1,14,16-trihydroxy-12-[2'-(4"-hydroxy-3"-methoxycyclohexyl)-1'-methylvinyl]-23,25-dimethoxy-16-(methylthiomethyl)-13,19,21,27-tetramethyl-11,28-dioxa-4-azatricyclo[22.3.1.0$^{4,9}$]octacos-18-ene-2,3,10-trione (faster isomer)

A sample of 10 mg (0.009 mmole) of 17-ethyl--1,14,16-trihydroxy-12-[2'-(4"-hydroxy-3"-methoxycyclohexyl)-1'-methylvinyl]-23,25-dimethoxy-16-(methylthiomethyl)-13,19,21,27-tetramethyl-11,28-dioxa-4-azatricyclo[22.3.1.0$^{4,9}$]octacos-18-ene-2,3,10-trione (faster isomer) was deprotected as in Part 2 of Example 3 to afford 6 mg (76%) of the title compound as a white solid whose $^1$H and $^{13}$C NMR spectra indicated that it was isomeric to the product of Example 10 at the 16 position; MASS SPECTRUM (FAB) m/e 860 (M+Li).

EXAMPLE 15

17-Ethyl-16-triethylsilyloxy-1,14-diihydroxy-12-[2'-(4"-triethylsilyloxy-3"-methoxycyclohexyl)-1'-methylvinyl]-23,25-dimethoxy-16-(methylthiomethyl)-13,19,21,27-tetramethyl-11,28-dioxa-4-azatricyclo[22.3.1.0$^{4,9}$]octacos-18-ene-2,3,10-trione (slower isomer)

Step 1

Further elution of the column in Part 1 of Example 13 using 10% ethyl acetate-hexane afforded 0.10 g (26%) the title compound as a white solid whose $^1$H and $^{13}$C NMR spectra were identical to those of the protected product from Example 10; MASS SPECTRUM (FAB) m/e 1088 (M+Li).

Step 2:
17-Ethyl-1,14,16-trihydroxy-12-[2'-(4"-hydroxy-3"-methoxycyclohexyl)-1'-methylvinyl]-23,25-dimethoxy-16-(methylthiomethyl)-13,19,21,27-tetramethyl-11,28-dioxa-4-azatricyclo[22.3.1.0$^{4,9}$]octacos-18-ene-2,3,10-trione (faster isomer)

A sample of 10 mg (0.009 mmole) of 17-ethyl-1,14,16-trihydroxy-12-[2'-(4"-hydroxy-3"-methoxycyclohexyl)-1'-methyl-vinyl]-23,25-dimethoxy-16-(methylthiomethyl)-13,19,21,27-tetramethyl-11,28-dioxa-4-azatricyclo[22.3.1.0$^{4,9}$]octacos-18-ene-2,3,10-trione (faster isomer) was deprotected as in Part 2 of Example 3 to afford 6 mg (76%) of the title compound as a white solid whose $^1$H and $^{13}$C NMR spectra were identical to those of the product of Example 10; MASS SPECTRUM (FAB) m/e 860 (M+Li).

EXAMPLE 16

17-Ethyl-1,14,16-trihydroxy-12-[2'-(4"-hydroxy-3"-methoxycyclohexyl)-1'-methylvinyl]-23,25-dimethoxy-16-phenyl-13,19,21,27-tetramethyl-11,28-dioxa-4-azatricyclo[22.3.1.0$^{4,9}$]octacos-18-ene-2,3,10-trione Prepared as in Example 4 except that a solution of phenyllithium was used in place of methyllithium to afford 0.029 g (33%) of the title compound as a white solid; MASS SPECTRUM (FAB) m/e 876 (M+Li).

EXAMPLE 17

17-Ethyl-1,14,16-trihydroxy-12-[2'-(4"-hydroxy-3"-methoxycyclohexyl)-1'-methylvinyl]-23,25-dimethoxy-16-furan-2-yl-13,19,21,27-tetramethyl-11,28-dioxa-4-azatricyclo[2-2.3.1.0$^{4,9}$]octacos-18-ene-2,3,10-trione Prepared as in Example 4 except that a solution of 2-lithiofuran was used in place of methyllithium to afford 0.021 g (24%) of the title compound as a white solid; MASS SPECTRUM (FAB) m/e 866 (M+Li).

(compound as a white solid; MASS SPECTRUM (FAB) m/e 858 (M+Li).)

EXAMPLE 18

17-Ethyl-1,14,16-trihydroxy-12-[2'-(4"'-hydroxy-3"-methoxycyclohexyl)-1'-methylvinyl]-14-triethylsilyloxy-23,25-dimethoxy-13,19,21,27-tetramethyl-2-(1-methyl)-11,28-dioxa-4-azatri-cyclo[22.3.1.0$^{4,9}$]octacos-18-ene-3,10,16-tetraone A solution of 0.100 g (0.1 mmole) of 17-ethyl-1-hydroxy-12-[2'-(4"'-triethylsilyloxy-3"-methoxycyclohexyl)-1'-methylvinyl]-14-triethylsilyloxy-23,25-dimethoxy-13,19,21,27-tetramethyl-11,28-dioxa-4-azatri-cyclo[22.3.1.0$^{4,9}$]octacos-18-ene-2,3,10,16-tetraone in dry THF was cooled to −78° C. Then 0.1 mL of a 3.0M solution of methylmagnesium bromide was added and the solution was allowed to warm to 0° C. The solution was acidified by addition of 0.1 mL of glacial acetic acid and the mixture was partitioned between ether and KHCO$_3$ solution. The ether layer was washed with KHCO$_3$ and brine, then dried over MgSO$_4$ and concentrated. The residue was dissolved in 2 mL of a 1:19 solution of 48% aqueous HF-acetonitrile and left stirring at room temperature for 1 h. The reaction was quenched with 1 mL of ethoxytrimethylsilane and concentrated under vacuum. The residue was purified by preparatory TLC (4 plates, 250 m) using 15% acetone-hexane to afford 61 Mg (73%) of the title compound as a white solid.

$^1$H NMR (CDCl$_3$, 300 MHz) δ0.7–1.1 (m, 16H), 1.22 (s, 3H), 1.25–2.5 (m), 2.59 (s, 1H), 2.7–3.1 (m, 3H), 3.2–3.6 (m), 3.63 (d, 1H), 3.76 (s, 1H), 4.35 (d, 1H), 4.45 (d, 1H), 4.80 (d, 1H), 4.95 (m, 2H), 5.29 (m, 1H); $^{13}$C NMR (CDCl$_3$, 300 MHz) δ84.1, 97.7, 127.9, 128.2, 133.6, 136.9, 168.6, 173.2, 212.4; MASS SPECTRUM (FAB) 814 (M+Li).

EXAMPLE 19

17-Ethyl-1,14,16-trihydroxy-12-[2'-(4"'-hydroxy-3"-methoxycyclohexyl)-1'-methylvinyl]-14-triethylsilyloxy-23,25-dimethoxy-13,19,21,27-tetramethyl-2-(2-propenyl)-11,28-dioxa-4-azatricyclo[22.3.1.0$^{4,9}$]octacos-18-ene-3,10,16-tetraone Prepared as in Example 18 except that a solution of allylmagnesium bromide was used in place of methylmagnesium bromide to afford 0.056 g (67%) of the title compound as a white solid; MASS SPECTRUM (FAB) m/e 839 (M+Li).

EXAMPLE 20

17-Ethyl-1,14-dihydroxy-12-[2'-(4"'-hydroxy-3"-methoxycyclohexyl)-1'-methylvinyl]-14-triethylsilyloxy-23,25-dimethoxy-13,19,21,27-tetramethyl-2-methenyl-11,28-dioxa-4-azatri-cyclo[22.3.1.0$^{4,9}$]octacos-18-ene-3,10,16-tetraone A solution of 0.100 g (0.1 mmole) of 17-ethyl-1-hydroxy-12-[2'-(4"'-triethylsilyloxy-3"-methoxycyclohexyl)-1'-methylvinyl]-14-triethylsilyloxy-23,25-dimethoxy-13,19,21,27-tetramethyl-11,28-dioxa-4-azatri-cyclo[22.3.1.0$^{4,9}$]octacos-18-ene-2,3,10,16-tetraone in dry THF was cooled to −78° C. Then 0.3 mL of a 1.0M solution of trimethylsilylmethylmagnesium bromide was added and the solution was allowed to warm to 0° C. until tlc (silica gel, 20% ethyl acetate-hexane) indicated that no starting material remained. The solution was acidified by addition of 0.1 mL of glacial acetic acid and the mixture was partitioned between ether and KHCO$_3$ solution. The ether layer was washed with KHCO$_3$ and brine, then dried over MgSO$_4$ and concentrated. The residue was dissolved in 2 mL of a 1:19 solution of 48% aqueous HF-acetonitrile and left stirring at room temperature for 1 h. The reaction was quenched with 1 mL of ethoxytrimethylsilane and concentrated under vacuum. The residue was purifed by preparatory TLC (4 plates, 250 m) using 15% acetone-hexane to afford 15 mg (18%) of the title compound as a white solid.

$^1$H NMR (CDCl$_3$, 300 MHz) δ0.7–1.1 (m, 16H), 1.25–2.5 (m), 2.59 (s, 1H), 2.7–3.1 (m, 3H), 3.2–3.6 (m), 3.63 (d, 1H), 3.76 (s, 1H), 4.35 (d, 1H), 4.45 (d, 1H), 4.80 (d, 1H), 4.95 (m, 2H), 5.29 (m, 1H), 6.2–6.3 (m, 2H); $^{13}$C NMR (CDCl$_3$, 300 MHz) d 84.1, 97.7, 126.8, 127.9, 128.2, 133.6, 136.9, 139.4, 164.9, 168.6, 195.9; MASS SPECTRUM (FAB) 796 (M+Li).

EXAMPLE 21

Product from intramolecular rearrangement of 17-Ethyl-1,14-hydroxy-12-[2'-(4"'-hydroxy-3"-methoxycyclohexyl)-1'-methylvinyl]-14-triethylsilyloxy-23,25-dimethoxy-13,19,21,27-tetramethyl-2-methenyl-11,28-dioxa-4-azatri-cyclo[22.3.1.0$^{4,9}$]octacos-18-ene-3,10,16-tetraone A solution of 0.025 g (0.126 mmole) of 17-ethyl-1,14-hydroxy-12-[2'-(4"'-hydroxy-3"-methoxycyclohexyl)-1'-methylvinyl]-14-triethylsilyloxy-23,25-dimethoxy-13,19,21,27-tetramethyl-2-methenyl-11,28-dioxa-4-azatri-cyclo[22.3.1.0$^{4,9}$]octacos-18-ene-3,10,16-tetraone in dichloromethane was left at room temperature for 24 h. TLC of the solution in 20% acetone-hexane indicated that a new, more polar product had formed and that this material no longer gave UV end-absorption characteristic of unsaturated carbonyl compounds. The solution was concentrated to dryness to afford 25 mg of the title compound as a pale yellow glass.

$^1$H NMR (CDCl$_3$, 300 MHz) δ0.7–1.1 (m, 16H), 1.25–2.5 (m), 2.59 (s, 1H), 2.7–3.1 (m, 3H), 3.2–3.6 (m), 3.63 (d, 1H), 4.20–4.50 m, 4H), 4.80 (d, 1H), 4.95 (m, 2H), 5.29 (m, 1H); $^{13}$C NMR (CDCl$_3$, 300 MHz) d 84.1, 127.9, 128.2, 133.6, 136.9, 168.6, 173.5; 204 (broad), 212.2; MASS SPECTRUM (FAB) 796 (M+Li).

EXAMPLE 22

Step 1:

17-Ethyl-12-[2'-(4"'-t-butyldimethylsilyloxy-3"-methoxycyclohexyl)-1'-methylvinyl]-14-t-butyldimethylsilyloxy-23,25-dimethoxy-13,19,21,27-tetramethyl-11,28-dioxa-4-azatri-cyclo[22.3.1.0$^{4,9}$]octacos-1,18-diene-2,3,10,16-tetraone A solution of DEAD-PPH$_3$ complex was prepared by dropwise addition of 13.8 mL (95 mmole) of diethyl azodicarboxylate to a solution of 30 g (114.5 mmole) of triphenylphosphine in 200 mL of dry THF. This solution was stirred at room temperature for 30 minutes, then cooled to 0° C. A solution of 34.1 g (31.6 mmole) of crude 17-ethyl-1-hydroxy-12-[2'-(4"'-t-butyldimethylsilyloxy-3"-methoxycyclohexyl)-1'-methylvinyl]-14-t-butyldimethylsilyloxy-23,25-dimethoxy-13,19,21,27-tetramethyl-11,28-dioxa-4-azatri-cyclo[22.3.1.0$^{4,9}$]octacos-18-ene-2,3,10,16-tetraone in 500 mL of dry THF was cooled to 0° C. and then the first solution of DEAD-PPH$_3$ was added at such a rate to keep the temperature of the solution below 10° C. After 4 h, the reaction was quenched by addition of 30 mL of H$_2$O and the solution was concentrated to about 100 mL volume under vacuum. The solution was partitioned between ether and water and the ether layer was washed two times with brine, dried over MgSO$_4$, and concentrated. The residue was crystallized from ether-hexane and filtered. The filtrate was concentrated and the oily residue was taken up in hexane and filtered a second time to remove residual triphenylphosphine oxide. The clear filtrate was concentrated to afford 35.2 g (100%) of the title compound as a pale yellow oil (that was contaminated with some residual triphenylphosphine).

$^1$H NMR (CDCl$_3$, 300 MHz) δ0.02–0.04 (s, 12H), 0.6–1.0 (m, 16H), 0.90 (s, 18H), 1.3–2.4 (m), 2.15 (s, 3H, 27-CH$_3$), 2.9 (m, 2H), 3.2–3.8 (m), 4.45 (m, 1H), 4.95 (m, 2H), 5.25 (d, 2H); $^{13}$C NMR (CDCl$_3$, 75 MHz) d 83.8, 97.5, 117, 128.0, 128.7, 133.4, 136.9, 145, 164.8, 168.9, 188.5; MASS SPECTRUM (FAB) 1008(M+Li).

Step 2:

17-Ethyl-14-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-1, 18-diene-2,3,10,16-tetraone A sample of 2.01 g (2.02 mmole) of 17-ethyl-12-[2'-(4''-t-butyldimethylsilyloxy-3''-methoxycyclohexyl)-1'-methylvinyl]-14-t-butyldimethylsilyloxy-23,25-dimethoxy-13,19,21,27-tetramethyl-11,28-dioxa-4-aza tricyclo[22.3.1.0$^{4,9}$]octacos-18-ene-2,3,10,16-tetraone was deprotected as in Part 2 of Example 3 to afford 1.46 g (94%) of the title compound as a white powder after lyophillization from benzene.

$^1$H NMR (CDCl$_3$, 300 MHz) δ0.6–1.0 (m, 16H), 1.3–2.4 (m), 2.15 (s, 3H, 27-CH$_3$), 2.9 (m, 2H), 3.2–3.8 (m), 4.45 (d, 1H), 4.95 (m, 2H), 5.25 (m, 2H); $^{13}$C NMR (CDCl$_3$, 75 MHz) d 83.8, 97.5, 117, 128.0, 128.7, 133.4, 136.9, 145, 164.8, 168.9, 188.5; MASS SPECTRUM (FAB) 1008(M+Li).

EXAMPLE 23

17-Ethyl-14-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step 1:

17-Ethyl-12-[2'-(4''-t-butyldimethylsilyloxy-3''-methoxycyclohexyl)-1'-methylvinyl]-14-t-butyldimethylsilyloxy-23,25-dimethoxy-13,19,21,27-tetramethyl-11,28-dioxa-4-azatri-cyclo[22.3.1.0$^{4,9}$]octacos-18-ene-2,3,10,16-tetraone A solution of 35.2 g (31.6 mmole) of crude 17-ethyl-12-[2'-(4''-t-butyldimethylsilyloxy-3''-methoxycyclohexyl)-1'-methylvinyl]-14-t-butyldimethylsilyloxy-23,25-dimethoxy-13,19,21,27-tetramethyl-11,28-dioxa-4-azatri-cyclo[22.3.1.0$^{4,9}$]octacos-1,18-diene-2,3,10,16-tetraone in 500 mL of dry THF was cooled to −90° C. under nitrogen. Then 150 mL of a 0.5M solution of KHBPH$_3$ in dry THF was added at such a rate so that the temperature did not rise above −78° C. After addition was complete, the solution was left stirring under nitrogen for 72 h, then was quenched by dropwise addition of methanol, again keeping the temperature of the solution below −75° C. The mixture was partitioned between ether and water and the ether layer was washed sequentially with KHCO$_3$ and brine, dried over MgSO$_4$, and concentrated. The residue was purified by flash chromatography (15 cm×40 cm) using 10% ethyl acetate-hexane to afford 11.28 g (35.7%) of recovered starting material. Further elution with 15% ethyl acetate-hexane afforded 14.13 g (45%) of the title compound as a white foam.

NMR (CDCl$_3$, 300 MHz) δ0.02–0.04 (s, 12H), 0.6–1.0 (m, 16H), 0.90 (s, 18H), 1.3–2.4 (m), 2.9 (m, 2H), 3.2–3.8 (m), 4.39 (d, 1H), 4.85 (d, 1H), 4.95 (m, 2H), 5.25 (d, 1H); $^{13}$C NMR (CDCl$_3$, 75 MHz) d 84.1, 122.5, 131.3, 132.2, 138.9, 165.9, 169.3, 200.4. 212; MASS SPECTRUM (FAB) 1010 (M+Li).

Step 2:

17-Ethyl-14-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A sample of 1.62 g (1.61 mmole) of 17-ethyl-12-[2'-(4''-t-butyldimethylsilyloxy-3''-methoxycyclohexyl)-1'-methylvinyl]-14-t-butyldimethylsilyloxy-23,25-dimethoxy-13,19,21,27-tetramethyl-11,28-dioxa-4-azatri-cyclo[22.3.1.0$^{4,9}$]octacos-18-ene-2,3,10,16tetraone was deprotected as in Part 2 of Example 3 to afford 0.962 g (77%) of the title compound as a white powder after lyophillization from benzene.

$^1$H NMR (CDCl$_3$, 300 MHz) δ0.6–1.0 (m, 16H), 1.3–2.4 (m), 2.9 (m, 2H), 3.2–3.8 (m), 4.39 (d, 1H), 4.85 (d, 1H), 4.95 (m, 2H), 5.25 (d, 1H); $^{13}$C NMR (CDCl$_3$, 75 MHz) d 84.1, 122.5, 131.3, 132.2, 138.9, 165.9, 169.3, 200.4. 212; MASS SPECTRUM (FAB) 782 (M+Li).

EXAMPLE 24

17-Ethyl-14-hydroxy-12-[2'-(4''-hydroxy-3''-methoxycyclohexyl)-1'-methylvinyl]-23,25-dimethoxy-13,19,21,epi-27-tetramethyl-11,28-dioxa-4-azatricyclo[22.3.1.0$^{4,9}$]octacos-18-ene-2,3,10,16-tetraone

Step 1:

17-Ethyl-12-[2'-(4''-t-butyldimethylsilyloxy-3''-methoxycyclohexyl)-1'-methylvinyl]-14-t-butyldimethylsilyloxy-23,25-dimethoxy-13,19,21,epi-27-tetramethyl-11,28-dioxa-4-azatri-cyclo[22.3.1.0$^{4,9}$]octacos-18-ene-2,3,10,16-tetraone Further elution of the column in Step 1 of Example 21 with 25% ethyl acetate-hexane afforded 1.36 g (4.3%) of the title compound as a white foam; MASS SPECTRUM (FAB) m/e 1010.

Step 2:

17-Ethyl-14-hydroxy-12-[2'-(4''-hydroxy-3''-methoxycyclohexyl)-1'-methylvinyl]-23,25-dimethoxy-13,19,21,epi-27-tetramethyl-11,28-dioxa-4-azatricyclo[22.3.1.0$^{4,9}$]octacos-18-ene-2,3,10,16-tetraone A sample of 0.043 g (0.042 mmole) of 17-ethyl-12-[2'-(4''-t-butyldimethylsilyloxy-3''-methoxycyclohexyl)-1'-methylvinyl]-14-t-butyldimethylsilyloxy-23,25-dimethoxy-13,19,21,epi-27-tetramethyl-11,28-dioxa-4-azatri-cyclo[22.3.1.0$^{4,9}$]octacos-18-ene-2,3,10,16-tetraone was deprotected as in Step 2 of Example 3 to afford 0.028 g (84%) of the title compound as a white powder after lyophillization from benzene; MASS SPECTRUM (FAB) m/e 782.

EXAMPLE 25

T-Cell Proliferation Assay

1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The various dilutions of the compound to be tested were then added in triplicate wells at 20 μl/well. The compound 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-aza-tricyclo[22.3.1.0$^{4,9}$]octacos-18-ene-2,3,10,16-tetraone was used as a standard. The culture plates were then incubated at 37° C. in a humidified atmosphere of 5% CO$_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass). After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results expressed as concentration of compound required to inhibit tritiated thymidine uptake of T-cells by 50%.

A selection of compounds were tested according to the previous procedure. The title compounds of the following Examples had activity in inhibiting the proliferation of T-cells in the aforementioned assay: 3, 6, 15, 20, 22, 23 and 24.

For determining antagonist activity, the foregoing procedure is modified in that dilutions of compounds are cultured with 17-ally-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (as a standard) at a concentration of 1.2 nM, a concentration which inhibits T cell proliferation by 100%, the concentration of compound required to reverse the inhibition obtained by the standard alone by 50% is measured, and the ED$_{50}$ value is determined.

A selection of compounds were tested according to the previous procedure. The title compounds of the following Examples had activity in reversing the inhibition of proliferation of T-cells by the standard in the aforementioned assay: 5, 7, 10, 11, 12, 15 and 17.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of formula I:

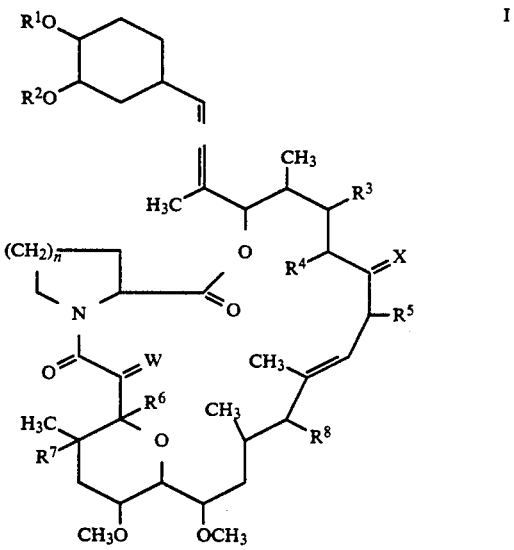

or a pharmaceutically acceptable salt thereof, wherein:
  $R^1$ is selected from:
  (1) hydrogen; and
  (2) $C_{1-4}$ alkanoyl;
  $R^2$ is selected from:
  (1) methyl; and
  (2) hydrogen;
  $R^3$ is hydrogen, hydroxy, or $C_{1-6}$alkoxy;
  $R^4$ is hydrogen, or $R^3$ and $R^4$ taken together form a double bond;
  $R^5$ is selected from:
  (1) methyl,
  (2) ethyl
  (3) propyl, and
  (4) allyl;
  $R^6$ is hydroxy or hydrogen;
  $R^7$ is hydrogen, or $R^6$ and $R^7$ taken together form a double bond;
  $R^8$ is hydrogen, hydroxy, or fluoro;
  W and X are independently selected from:
  (1) oxo,
  (2) (H, OH),
  (3) (OH, $R^9$), wherein $R^9$ is selected from:
    (a) $C_{1-6}$ alkyl,
    (b) $C_{2-6}$ alkenyl, (c) —CH$_2$—SO$_m$—C$_{1-6}$ alkyl, wherein m is 0, 1 or 2,
(d) —CH$_2$S(C$_{1-6}$ alkyl)$_2$$^+$M$^-$, wherein M$^-$ is a negative counterion selected from: chloro, bromo, iodo,
(e) phenyl,
(f) furanyl,
(4) =CR$^{10}$R$^{11}$, wherein R$^{10}$ and R$^{11}$ are independently selected from:
(a) hydrogen,
(b) C$_{1-6}$ alkyl,
(c) C$_{2-6}$ alkenyl,
(d) —SO$_m$—C$_{1-6}$ alkyl, wherein m is as defined above;
with the proviso that W and X are not simultaneously oxo, (H, OH), or combinations thereof;
n is 1 or 2.

2. The compound according to claim 1 wherein the absolute configuration of formula I is as defined in formula III:

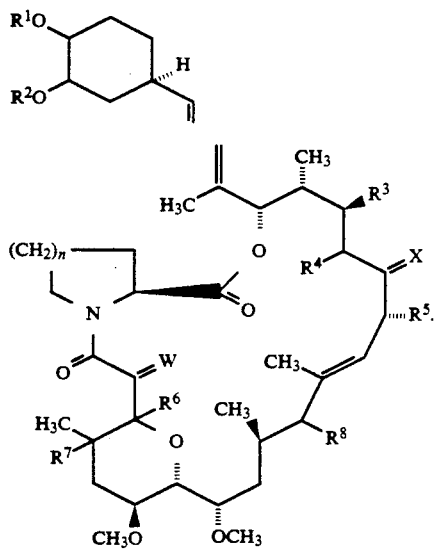

III

3. A compound which is selected from the group consisting of:
17-Ethyl-1,14,16-trihydroxy-12-[2'-(4"-hydroxy-3"-methoxycyclohexyl)-1'-methylvinyl]-23,25-dimethoxy-16-methyl-13,19,21,27-tetramethyl-11,28-dioxa-4-azatricyclo[22.3.1.0$^{4,9}$]octacos-18-ene-2,3,10-trione; (1)
17-Ethyl-1,14,16-trihydroxy-12-[2'-(4"-hydroxy-3"-methoxycyclohexyl)-1'-methylvinyl]-23,25-dimethoxy-16-methyl-13,19,21,27-tetramethyl-11,28-dioxa-4-azatricyclo[22.3.1.0$^{4,9}$]octacos-18-ene-2,3,10-trione; (2)
17-Ethyl-1,14,16-trihydroxy-12-[2'-(4"-hydroxy-3'-methoxycyclohexyl)-1'-methylvinyl]-23,25-dimethoxy-16-butyl-13,19,21,27-tetramethyl-11,28-dioxa-4-azatricyclo[22.3.1.0$^{4,9}$]octacos-18-ene-2,3,10-trione; (3)
17-Ethyl-1,14-dihydroxy-12-[2'-(4"-hydroxy-3"-methoxycyclohexyl)-1'-methylvinyl]-23,25-dimethoxy-16-butyl-13,19,21,27-tetramethyl-16-methenyl-11,28-dioxa-4-azatricyclo[22.3.1.0$^{4,9}$]octacos-18-ene-2,3,10-trione; (4)
17-Ethyl-1,14-dihydroxy-12-[2'-(4"-hydroxy-3"-methoxycyclohexyl)-1'-methylvinyl]-23,25-dimethoxy-16-butyl-13,19,21,27-tetramethyl-16-(2-butenyl)-11,28-dioxa-4-azatricyclo[22.3.1.0$^{4,9}$]octacos-18-ene-2,3,10-trione; (5)
17-Ethyl-1,14-dihydroxy-12-[2'-(4"-hydroxy-3"-methoxycyclohexyl)-1'-methylvinyl]-23,25-dimethoxy-16-propenyl-13,19,21,27-tetramethyl-11,28-dioxa-4-azatricyclo[22.3.1.0$^{4,9}$]octacos-18-ene-2,3,10-trione; (6)
17-Ethyl-1,14,16-trihydroxy-12-[2'-(4"-hydroxy-3'-methoxycyclohexyl)-1'-methylvinyl]-23,25-dimethoxy-16-(methylthiomethyl)-13,19,21,27-tetramethyl-11,28-dioxa-4-azatricyclo[22.3.1.0$^{4,9}$]octacos-18-ene-2,3,10-trione; (7)
17-Ethyl-1,14,16-trihydroxy-12-[2'-(4"-hydroxy-3"-methoxycyclohexyl)-1'-methylvinyl]-23,25-dimethoxy-16-(methylsulfinylmethyl)-13,19,21,27-tetramethyl-11,28-dioxa-4-azatricyclo[22.3.1.0$^{4,9}$]octacos-18-ene-2,3,10-trione; (8)
17-Ethyl-1,14,16-trihydroxy-12-[2'-(4"-hydroxy-3'-methoxycyclohexyl)-1'-methylvinyl]-23,25-dimethoxy-16-(methylsulfinylmethenyl)-13,19,21,27-tetramethyl-11,28-dioxa-4-azatricyclo[22.3.1.0$^{4,9}$]octacos-18-ene-2,3,10-trione; (9)
17-Ethyl-1,14,16-trihydroxy-12-[2'-(4"-hydroxy-3"-methoxycyclohexyl)-1'-methylvinyl]-23,25-dimethoxy-16-phenyl-13,19,21,27-tetramethyl-11,28-dioxa-4-azatricyclo[22.3.1.0$^{4,9}$]octacos-18-ene-2,3,10-trione; (10)
17-Ethyl-1,14,16-trihydroxy-12-[2'-(4"-hydroxy-3"-methoxycyclohexyl)-1'-methylvinyl]-23,25-dimethoxy-16-phenyl-13,19,21,27-tetramethyl-11,28-dioxa-4-azatricyclo[2 2.3.1.0$^{4,9}$]octacos-18-ene-2,3,10-trione; (11)
17-Ethyl-14-hydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-1,18-diene-2,3,10,16-tetraone; (12)
17-Ethyl-14-hydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (13)
17-Ethyl-14-hydroxy-12-[2'-(4"-hydroxy-3"-methoxycyclohexyl)-1'-methylvinyl]-23,25-dimethoxy-13,19,21, epi-27-tetramethyl-11,28-dioxa-4-azatricyclo[22.3.1.0$^{4,9}$]octacos-18-ene-2,3,10,16-tetraone (14).

4. A compound which is:

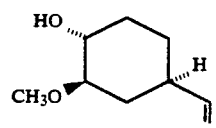

-continued

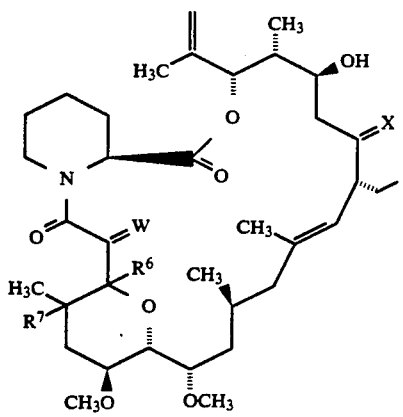

wherein $R^6$, $R^7$, X and W are selected from the following combinations of substituents:

|  | $R^6$ | $R^7$ | X | W |
|---|---|---|---|---|
| (a) | (double bond) |  | $CH_2$ | O |
| (b) | (double bond) |  | O | $CH_2$ |
| (c) | H | H | $CH_2$ | O |
| (d) | H | H | O | $CH_2$ |
| (e) | H | H | (OH, $CH_3$) | O |
| (f) | H | H | (OH, $CH_3$) | $CH_2$ |
| (g) | H | H | (OH, $CH_3$) | O |
| (h) | H | H | (OH, $CH_3$) | $CH_2$. |

5. The compound of claim 4 which is:

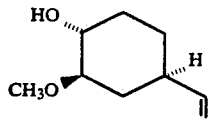

-continued

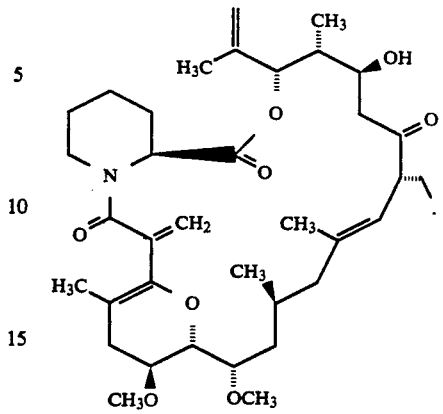

6. The compound of claim 4 which is:

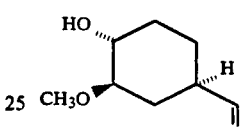

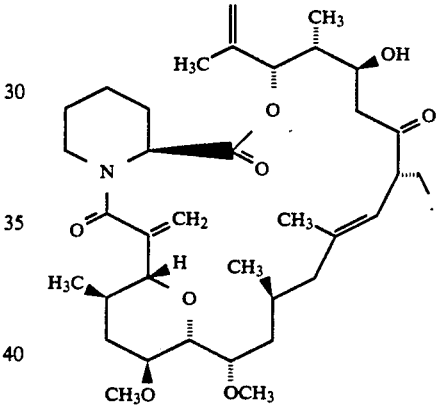

7. A pharmaceutical composition comprising a pharmaceutical carrier and a therapeutically effective amount of the compound of claim 1.

8. A method for the treatment of immunoregulatory disorders or diseases comprising the administration to a mammalian species in need of such treatment of an effective amount of the compound of claim 1.

* * * * *